(12) United States Patent
O'Keefe

(10) Patent No.: US 11,545,247 B2
(45) Date of Patent: *Jan. 3, 2023

(54) MEDICATION COMPLIANCE METHODS, DEVICES, AND SYSTEMS

(71) Applicant: LONGEVITY HEALTH CORP., Sheridan, WY (US)

(72) Inventor: Sean O'Keefe, Bonita, CA (US)

(73) Assignee: LONGEVITY HEALTH CORP., Sheridan, WY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/226,045

(22) Filed: Apr. 8, 2021

(65) Prior Publication Data
US 2021/0295972 A1   Sep. 23, 2021

Related U.S. Application Data

(63) Continuation-in-part of application No. 17/063,580, filed on Oct. 5, 2020, which is a continuation of
(Continued)

(51) Int. Cl.
*G16H 20/10* (2018.01)
*A61J 7/00* (2006.01)
(Continued)

(52) U.S. Cl.
CPC ............ *G16H 20/10* (2018.01); *A61J 1/1412* (2013.01); *A61J 1/1437* (2013.01); *A61J 7/0076* (2013.01); *A61J 7/0436* (2015.05); *A61J 7/0472* (2013.01); *A61J 7/0481* (2013.01); *B65D 51/245* (2013.01); *B65D 55/14* (2013.01); *G06V 40/13* (2022.01); *G07C 9/00563* (2013.01);
(Continued)

(58) Field of Classification Search
CPC ........ G16H 20/10; G16H 20/13; G16H 40/63; G16H 40/67; G16H 15/00; A61J 1/1412; A61J 1/1437; A61J 7/0076; A61J 7/0436; A61J 7/0472; A61J 7/0481; A61J 1/03; A61J 7/0418; A61J 2200/30; A61J 2205/60; B65D 51/245; B65D 55/14; G06V 40/13; G06V 40/12; G07C 9/00563; G07C 9/00896; G07C 9/37; G07C 2209/14; G07C 9/00912; G08B 7/00; H04B 1/38
USPC .................................................... 340/539.12
See application file for complete search history.

(56) References Cited

U.S. PATENT DOCUMENTS 6,382,416 B1 *  5/2002  Gainey ................. A61J 1/1437
                                                       206/317
10,380,327 B1 *  8/2019  Bradley ................. G06F 3/147
(Continued)

*Primary Examiner* — Hirdepal Singh
(74) *Attorney, Agent, or Firm* — Entralta P.C.; James F. Fleming; Peter D. Weinstein

(57) ABSTRACT

*Cannabis*, much like medications, requires secure containment. It is particularly important to prevent access to *Cannabis* to children, elderly, or others for whom the *Cannabis* is not prescribed, designated, or legally permitted. Provided herein are medication tracking and securement devices, systems, platforms, and methods configured to be used with or in place of commercial standard medicine bottles. The wireless tracking and communications elements of the present disclosure are configured to prevent medication theft, overdosing, medication loss, and prescription noncompliance.

6 Claims, 15 Drawing Sheets

Related U.S. Application Data application No. 15/901,700, filed on Feb. 21, 2018, now Pat. No. 10,796,790.

(60) Provisional application No. 62/461,908, filed on Feb. 22, 2017.

(51) Int. Cl.

| | | |
|---|---|---|
| *A61J 7/04* | (2006.01) | |
| *G07C 9/00* | (2020.01) | |
| *G16H 20/13* | (2018.01) | |
| *A61J 1/14* | (2006.01) | |
| *B65D 51/24* | (2006.01) | |
| *B65D 55/14* | (2006.01) | |
| *G08B 7/00* | (2006.01) | |
| *G06V 40/13* | (2022.01) | |
| *A61J 1/03* | (2006.01) | |
| *G07C 9/37* | (2020.01) | |
| *H04B 1/38* | (2015.01) | |

(52) U.S. Cl.
CPC .......... *G07C 9/00896* (2013.01); *G08B 7/00* (2013.01); *G16H 20/13* (2018.01); *A61J 1/03* (2013.01); *A61J 7/0418* (2015.05); *A61J 2200/30* (2013.01); *A61J 2205/60* (2013.01); *G07C 9/37* (2020.01); *G07C 2209/14* (2013.01); *H04B 1/38* (2013.01)

(56) References Cited

U.S. PATENT DOCUMENTS

2016/0048657 A1\* 2/2016 LeBrun .................. A61J 1/1412
705/2
2018/0086518 A1\* 3/2018 Charm ................. B65D 43/163
2019/0122463 A1\* 4/2019 Romero ............. G07C 9/00896

\* cited by examiner

MEDICATION COMPLIANCE METHODS, DEVICES, AND SYSTEMS

CROSS-REFERENCE OF RELATED APPLICATIONS

This application is a continuation-in-part of U.S. application Ser. No. 17/063,580 filed Oct. 5, 2020, which is a continuation application of Ser. No. 15/901,700 filed Feb. 21, 2018 which claims the benefit of U.S. Provisional Application No. 62/461,908, filed Feb. 22, 2017, which application is incorporated herein by reference.

BACKGROUND OF THE INVENTION

Medication has become ubiquitous as over 4 billion prescriptions are filled in the United States every year. Addiction, overuse, misuse, and theft of such prescriptions and over-the-counter medications cause significant social and economic issues. It is estimated that more Americans died of drug overdoses in 2016 than died in the entirety of the Vietnam War. Additionally, it has been estimated that more people die from drug overdoses than car crashes, firearms, suicide, and other crimes and disease combined. Further, consumers and tax payers incur multiple millions of dollars in costs associated with medication loss, replacement, overdose, hospitalization, and the continued care required for the addicted and afflicted for withdrawal symptoms, emergency room visits, hospitalization, serious side effects, illness, and death.

Proper medication containment and security has been shown to reduce the prevalence of intentional and accidental overdose, addiction formation, and medication theft. As some prescription medications, such as fentanyl, are as powerful as, or more potent than, many common illicit drugs, medication security has been shown to prevent the theft and resale of such medications within the illegal drug market.

Many current pharmaceutical and pharmacy companies employ Child Resistant Packaging (CRP) to prevent accidental overdose in children. As CRP medication packaging devices must conform to international qualifications, many such bottle designs are similarly designed.

Another source of preventable illness is found in the lack of adherence to many prescribed medications. As many treatment regimens require multiple individual medications, each with a unique schedule and dosage, mistaken nonadherence is prevalent as well. Approximately 50% to 70% of written prescriptions are taken to the pharmacy, and 48% to 66% are picked up. Of those picked up, 25% to 30% are taken correctly and 15% to 20% are refilled as prescribed.

*Cannabis* is a plant of the Cannabaceae family and contains more than eighty biologically active chemical compounds. The most commonly known compounds are delta-9-tetrahydrocannabinol (THC) and cannabidiol (CBD). Cannabidiol (CBD) is a natural, non-psychoactive phytocannabinoid that occurs naturally in *Cannabis* plants, including hemp. There are some 113 identified cannabinoids in *Cannabis* plants and CBD accounts for up to 40% of the *Cannabis* plant's extract. CBD is known to act on cannabinoid receptors and several other neurotransmitters in the body. Clinical research has found that CBD showed efficacy in the treatment of different diseases and syndromes including anxiety, cognition, movement disorders, and pain. The side effects of long-term use of CBD include somnolence, decreased appetite, diarrhea, fatigue, malaise, weakness, and sleeping problems. Food and beverage items can be infused with CBD as a means of ingesting the substance.

Delta-9-tetrahydrocannabinol (Δ9-THC), better known to *Cannabis* users simply as THC, is the marijuana plant's primary component for causing psychoactive effects. It was listed under Schedule I in 1971, but reclassified to Schedule II in 1991 following a recommendation from the WHO. The market for consumables that include CBD and/or THC has grown as states in the U.S. have liberalized their laws against *Cannabis* use.

Edibles are increasingly popular forms of nonmedical *Cannabis* and include baked goods, candies and beverages. Legal edibles are available in several US states and became commercially available in Canada in late 2019. Despite their appearance, *Cannabis* edibles (e.g. gummies and chocolate bars infused with THC) can be dangerous. A recent article published in the Canadian Medical Association Journal described the risks associated with *Cannabis* edibles for different users and found that young people are among the most at-risk when it comes to overconsumption and accidental ingestion. At particular risk are children and pets as many edibles look like candy and other appetizing food and drink.

Unlike inhaled *Cannabis*, ingested *Cannabis* must be digested first before being absorbed. This delay can lead inexperienced users to inadvertently overconsume because they might not feel the intended effects immediately. For this reason, among others, young and old adults are at greater risk of overconsumption and accidental ingestion of *Cannabis* edibles.

Despite the dangers that *Cannabis* products present, most *Cannabis* dispensaries do not provide products in secure containers. Typical dispensary packaging includes plastic or glass jars for plant components (e.g. flowers). Edibles and concentrates are often sold in small plastic bags or decorative jars. It is worth noting that conventional child-resistant pill bottles (when provided) can be ineffective. Reports demonstrate that kids can often open child-resistant pill bottles in seconds, putting them at risk of accidental poisoning.

Accordingly, there is a need for improved, secure containers for *Cannabis* and *Cannabis* products including edibles. A smart medicament container (or cap) should secure a *Cannabis* product from being tampered with. It should allow a user to maintain a record of consumption. It should be child-resistant but easy to use for older adults. Further, it should be compliant with regulatory requirements.

SUMMARY OF THE INVENTION

Although current medication tracking and securement devices and systems are currently available, none are configured to be used with commercial standard medicine bottles. As such commercial medicine bottles are easily disposable and contain prescription dosage and refill information, employing the devices, systems, and platforms herein enable for safe, secure, and constant medication treatments. Additionally, the wireless and dosage managing capabilities of the present disclosure are configured to prevent medication theft, overdosing, medication loss, and prescription noncompliance.

Provided herein is a smart medicament container cap comprising: a housing comprising a bottle engagement coupling configured to engage with a medicine bottle, a medicine bottle sleeve, or both; a security input connected to the housing and configured to receive a security data; an actuator connected to the housing; a compression plate connected to the actuator and engaged with the housing by a slideable coupling; and a digital processing device connected to the housing, wherein the digital processing device is configured to receive the security data from a security input and to command the actuator in response to at least the security data; wherein the bottle engagement coupling, the actuator, and the compression plate are configured to temporarily prevent access to contents within the medicine bottle, the medicine bottle sleeve, or both. In some embodiments, the housing comprises a first cavity having an interior housing surface and an exterior housing surface. In some embodiments, the interior housing surface comprises the bottle engagement coupling. In some embodiments, the exterior housing surface comprises the bottle engagement coupling. In some embodiments, the bottle engagement coupling comprises a plurality of bottle engagement couplings comprising 1 to 10 bottle engagement couplings. In some embodiments, the plurality of bottle engagement couplings comprises a radial array of bottle engagement couplings. In some embodiments, the medicine bottle comprises a commercial medicine bottle. In some embodiments, the commercial medicine bottle comprises a push-to-lock medicine bottle, a pill bottle, a liquid medicine bottle, a child-resistant medicine bottle, or any combination thereof. In some embodiments, the security input comprises a keyhole, a button, a fingerprint scanner, a biometric scanner, a retinal scanner, a camera, a microphone, a GPS sensor, a Wi-Fi sensor, a Bluetooth sensor, an RFID sensor, an NFC sensor, or any combination thereof. In some embodiments, the actuator comprises a motor, a servomotor, a linear actuator, a solenoid, a gear, a sprocket, a nut, a belt, a chain, a bearing, a spring, a shaft, a lead screw, a coupling, or any combination thereof. In some embodiments, the connection between the housing and at least one of the security input, the actuator, and the digital processing device comprises a rigid connection. In some embodiments, the slideable coupling between the compression plate and the housing comprises a tongue, a groove, a bearing, a gear, a pulley, a slot, or any combination thereof. In some embodiments, the digital processing device further comprises a wireless communication device configured to receive a wireless signal and transmit a communications signal to the digital processing device, and wherein the communication signal is based on the wireless signal. In some embodiments, the wireless communication device comprises a Wi-Fi sensor, a Bluetooth sensor, an RFID sensor, an NFC sensor, or any combination thereof. In some embodiments, the wireless signal comprises a medication name, a medical ailment, a medication dosage, a medication period, a medication interval, a doctor name, a patient name, a prescription date, a prescription number, a prescription barcode, a refill date, a number of refills, a pill size, a pill color, or any combination thereof. In some embodiments, the cap further comprises a memory connected to the housing. In some embodiments, the memory is configured to store at least the wireless signal. In some embodiments, the memory is configured to store a usage data, wherein the usage data comprises at least a time and date the command. In some embodiments, the communications signal further comprises the usage data. In some embodiments, the cap further comprises an energy storage device connected to the housing. In some embodiments, the energy storage device is replaceable, rechargeable or both. In some embodiments, the cap further comprises a charging port connected to the energy storage device. In some embodiments, the cap further comprises an indicator connected to the housing. In some embodiments, the indicator comprises a light, a screen, a reel, a knob, a dial, a gauge, a speaker, a screen, or any combination thereof. In some embodiments, the digital processing device is further configured to initiate the indicator in response to at least the security data. In some embodiments, the cap further comprises at least one of a programing button and a power button. In some embodiments, the digital processing device is further configured to detect initiation of at least the programming button and the power button. In some embodiments, the cap further comprises a display screen. In some embodiments, the display screen is connected to the housing. In some embodiments, the digital processing device is further configured to transmit a display data to the display screen. In some embodiments, the cap further comprises comprising a label. In some embodiments, the cap further comprises an environmental sensor comprising a thermometer, an accelerometer, a barometer, a magnetic sensor, a motion sensor, or any combination thereof.

Another aspect provided herein is a platform comprising: a smart medicament container cap comprising: a housing comprising a bottle engagement coupling configured to engage with a medicine bottle, a medicine bottle sleeve, or both; an actuator connected to the housing; and a compression plate connected to the actuator and engaged with the housing by a slideable coupling; wherein the bottle engagement coupling, the actuator, and the compression plate are configured to temporarily prevent access to contents within the medicine bottle, the medicine bottle sleeve, or both; a mobile processor configured to provide a mobile application comprising: a software module configured to receive a user medical information; a storage module configured to store the user medical information; a reception module configured to receive an instruction from a user; a transmission module configured to transmit a wireless signal based at least on the instruction and the user medical information; and a digital processing device in communication with the smart medicament container cap and the mobile processor, the digital processing device comprising: at least one processor; an operating system configured to perform executable instructions; a memory; a wireless communication device; and a computer program including instructions executable by the digital processing device to create an application comprising: a communication module configured to receive a wireless signal; and a command module configured to command the actuator in response to at least the wireless signal. In some embodiments, the digital processing device is separate and distinct from at least one of the cap, the medicine bottle, and the pill sleeve. In some embodiments, the digital processing device is permanently or removably connected to the cap or the pill sleeve. In some embodiments, the digital processing device is rigidly connected to, or integrated within, the cap or the pill sleeve. In some embodiments, the housing comprises a first cavity having an interior housing surface and an exterior housing surface. In some embodiments, the interior housing surface comprises the bottle engagement coupling. In some embodiments, the exterior housing surface comprises the bottle engagement coupling. In some embodiments, the bottle engagement coupling comprises a plurality of bottle engagement couplings comprising 1 to 10 bottle engagement couplings. In some embodiments, the plurality of bottle engagement couplings comprises a radial array of bottle engagement couplings. In some embodiments, the medicine bottle comprises a commercial medicine bottle. In some embodiments, the commercial medicine bottle comprises a push-to-lock medicine bottle, a pill bottle, a liquid medicine bottle, a child-resistant medicine bottle, or any combination thereof. In some embodiments, the actuator comprises a motor, a servomotor, a linear actuator, a solenoid, a gear, a sprocket, a nut, a belt, a chain, a bearing, a spring, a shaft, a lead screw, a coupling, or any combination thereof. In some embodiments, the slideable coupling comprises a tongue, a groove, a bearing, a gear, a pulley, a slot, or any combination thereof. In some embodiments, the cap further comprises a label. In some embodiments, the wireless communication device comprises a Wi-Fi sensor, a Bluetooth sensor, an RFID sensor, or any combination thereof. In some embodiments, the wireless signal comprises a medication name, a medical ailment, a medication dosage, a medication period, a medication interval, a doctor name, a patient name, a prescription date, a prescription number, a prescription barcode, a refill date, a number of refills, a pill size, a pill color, or any combination thereof. In some embodiments, the platform further comprises a security input configured to receive a security data. In some embodiments, the communication module is further configured to receive the security data from the security input. In some embodiments, the command module is further configured to command the actuator in response to the security data. In some embodiments, the security input comprises a keyhole, a button, a fingerprint scanner, a biometric scanner, a retinal scanner, a microphone, a GPS sensor, a Wi-Fi sensor, a Bluetooth sensor, an RFID sensor, a NFC sensor, or any combination thereof. In some embodiments, the memory is configured to store the input signal. In some embodiments, at least one of the cap and the digital processing device further comprise an energy storage device. In some embodiments, the energy storage device is replaceable, rechargeable, or both. In some embodiments, at least one of the cap and the digital processing device further comprises a charging port. In some embodiments, at least one of the cap and the digital processing device further comprise an indicator. In some embodiments, the indicator comprises a light, a screen, a reel, a knob, a dial, a gauge, a speaker, a screen, or any combination thereof. In some embodiments, the command module is further configured to initiate the indicator in response to at least the wireless signal. In some embodiments, at least one of the cap and the digital processing device further comprise at least one of a programing button and a power button. In some embodiments, the communication module configured to receive a signal from of at least one of the programming button and the power button. In some embodiments, at least one of the cap and the digital processing device further comprise a display screen. In some embodiments, the command module is further configured to transmit a display data to the display screen. In some embodiments, the user medical information comprises at least one of a user name, a medication name, a medical ailment, a medication dosage, a medication period, a medication interval, a doctor name, a prescription date, a pill size, and a pill color, and a patient voice pattern. In some embodiments, the communication module is further configured to transmit a dosing data based at least on the command. In some embodiments, the transmission module is further configured to receive the dosing data. In some embodiments, at least one of the memory and the storage module is configured to store the dosing data. In some embodiments, the mobile application further comprises a medication ordering module configured to order a medicament in response to at least the dosing data. In some embodiments, the transmission module is further configured to transmit a dosing alert. In some embodiments, the communication module is further configured to receive the dosing alert. In some embodiments, the platform comprises two or more caps, wherein each cap is associated with different user medical information. In some embodiments, the platform further comprises the medicine bottle sleeve. In some embodiments, the medicine bottle sleeve comprises a bottle containment cavity comprising an interior sleeve surface and an exterior sleeve surface. In some embodiments, the bottle containment cavity has an inner diameter configured to surround at least a portion of the medicine bottle. In some embodiments, the medicine bottle comprises a commercial medicine bottle. In some embodiments, the commercial medicine bottle comprises a push-to-lock medicine bottle, a pill bottle, a liquid medicine bottle, a child-resistant medicine bottle, or any combination thereof. In some embodiments, the medicine bottle sleeve comprises a sleeve engagement appendage configured to engage with the bottle engagement coupling. In some embodiments, the interior housing surface comprises the sleeve engagement appendage. In some embodiments, the exterior housing surface comprises the sleeve engagement appendage. In some embodiments, the sleeve engagement appendage comprises 1 to 10 sleeve engagement appendages. In some embodiments, the sleeve engagement appendage comprises a radial array of sleeve engagement appendages. In some embodiments, at least one of the medicine bottle sleeve and the cap further comprise an environmental sensor comprising a thermometer, an accelerometer, a barometer, a magnetic sensor, or any combination thereof.

Another aspect provided herein is a system comprising: a security input configured to receive a security data; a digital processing device connected to the housing, wherein the digital processing device is configured to receive the security data from a security input and to command the actuator in response to at least the security data; a medicine bottle sleeve comprising a sleeve engagement appendage; and a smart medicament container cap comprising: a housing comprising a bottle engagement coupling configured to engage with the sleeve engagement appendage; an actuator connected to the housing; and a compression plate connected to the actuator and engaged with the housing by a slideable coupling; wherein the bottle engagement coupling, the actuator, and the compression plate are configured to temporarily prevent access to contents within the medicine bottle, the medicine bottle sleeve, or both. In some embodiments, at least one of the digital processing device and the security input are separate and distinct from at least one of the cap and the pill sleeve. In some embodiments, at least one of the digital processing device and the security input are permanently or removably connected the cap or the pill sleeve. In some embodiments, at least one of the digital processing device and the security input are rigidly connected to, or integrated within, the cap or the pill sleeve. In some embodiments, the housing comprises a cavity having an interior housing surface and an exterior housing surface. In some embodiments, the interior housing surface comprises the bottle engagement coupling. In some embodiments, the exterior housing surface comprises the bottle engagement coupling. In some embodiments, the bottle engagement coupling comprises a plurality of bottle engagement couplings comprising 1 to 10 bottle engagement couplings. In some embodiments, the plurality of bottle engagement couplings comprises a radial array of bottle engagement couplings. In some embodiments, the medicine bottle sleeve comprises a bottle containment cavity having an interior sleeve surface and an exterior sleeve surface. In some embodiments, the bottle containment cavity has an inner diameter configured to surround at least a portion of a medicine bottle. In some embodiments, the medicine bottle comprises commercial medicine bottle comprising a push-to-lock medicine bottle, a pill bottle, a liquid medicine bottle, a child-resistant medicine bottle, or any combination thereof. In some embodiments, the interior sleeve surface comprises the sleeve engagement appendage. In some embodiments, the exterior sleeve surface comprises the sleeve engagement recess. In some embodiments, the sleeve engagement recess comprises 1 to 10 sleeve engagement appendages. In some embodiments, the sleeve engagement recess comprises a radial array of sleeve engagement appendages. In some embodiments, the security input comprises a keyhole, a button, a fingerprint scanner, a biometric scanner, a retinal scanner, a camera, a microphone, a GPS sensor, a Wi-Fi sensor, a Bluetooth sensor, an RFID sensor, a NFC sensor, or any combination thereof. In some embodiments, the actuator comprises a motor, a servomotor, a linear actuator, a solenoid, a gear, a sprocket, a nut, a belt, a chain, a bearing, a spring, a shaft, a lead screw, a coupling, or any combination thereof. In some embodiments, the slideable coupling between the compression plate and the housing comprises a tongue, a groove, a bearing, a gear, a pulley, a slot, or any combination thereof. In some embodiments, the digital processing device further comprises a wireless communication device configured to receive a wireless signal. In some embodiments, the wireless communication device comprises a Wi-Fi sensor, a Bluetooth sensor, an RFID sensor, an NFC sensor, or any combination thereof. In some embodiments, the wireless signal comprises a medication name, a medical ailment, a medication dosage, a medication period, a medication interval, a doctor name, a patient name, a prescription date, a prescription number, a prescription barcode, a refill date, a number of refills, a pill size, a pill color, or any combination thereof. In some embodiments, the system further comprises a memory. In some embodiments, the memory is configured to store at least the wireless signal. In some embodiments, the memory is permanently or removably connected the cap or the pill sleeve. In some embodiments, the memory is rigidly connected to or integrated within the cap or the pill sleeve. In some embodiments, the system further comprises an energy storage device. In some embodiments, the energy storage device is permanently or removably connected the cap or the pill sleeve. In some embodiments, the energy storage device is rigidly connected to or integrated within the cap or the pill sleeve. In some embodiments, the system further comprises a charging port connected to the energy storage device. In some embodiments, the energy storage device is replaceable, rechargeable or both. In some embodiments, the system further comprises an indicator rigidly connected to or integrated within the cap or the pill sleeve. In some embodiments, the indicator comprises a light, a screen, a reel, a knob, a dial, a gauge, a speaker, a screen, or any combination thereof. In some embodiments, the digital processing device is further configured to initiate the indicator in response to at least the security data. In some embodiments, the system further comprises at least one of a programing button and a power button. In some embodiments, at least one of a programing button and a power button are rigidly connected to or integrated within the cap or the pill sleeve. In some embodiments, the digital processing device is further configured to detect initiation of at least the programming button and the power button. In some embodiments, the system further comprises a display screen. In some embodiments, the display screen is rigidly connected to or integrated within the cap or the pill sleeve. In some embodiments, the digital processing device is further configured to transmit a display data to the display screen. In some embodiments, the at least one of the cap and the sleeve further comprise a label. In some embodiments, at least one of the cap and the sleeve further comprise an environmental sensor comprising a thermometer, an accelerometer, a barometer, a magnetic sensor, or any combination thereof.

Another aspect provided herein is a platform comprising: a medicine cabinet: a smart cabinet security device comprising a housing comprising a cabinet engagement coupling configured to engage with the medicine cabinet; and an electromagnetic actuator connected to the housing; wherein the cabinet engagement coupling, and the actuator are configured to temporarily prevent access to contents within medicine cabinet; a mobile processor configured to provide a mobile application comprising: a software module configured to receive a user medical information; a storage module configured to store the user medical information; a reception module configured to receive an instruction from a user; and a transmission module configured to transmit a wireless signal based at least on the instruction and the user medical information; and a digital processing device in communication with the smart cabinet security device and the mobile processor, the digital processing device comprising: at least one processor; an operating system configured to perform executable instructions; a memory; a wireless communication device; and a computer program including instructions executable by the digital processing device to create an application comprising: a communication module configured to receive a wireless signal; and a command module configured to command the actuator in response to at least the wireless signal. In some embodiments, the digital processing device is separate and distinct from the smart cabinet security device. In some embodiments, the digital processing device is permanently or removably connected to the smart cabinet security device. In some embodiments, the digital processing device is rigidly connected to or integrated within the smart cabinet security device. In some embodiments, the cabinet engagement coupling comprises a plurality of cabinet engagement couplings comprising 1 to 10 cabinet engagement couplings. In some embodiments, the cabinet engagement coupling comprises at least one of an adhesive, a tape, an epoxy, a cement, a screw, a bolt, a nut, a nail, a security screw, a security seal, a band, and a tie. In some embodiments, the medicine cabinet comprises a commercial medicine cabinet. In some embodiments, the actuator comprises a motor, a servomotor, a linear actuator, a solenoid, a gear, a sprocket, a nut, a belt, a chain, a bearing, a spring, a shaft, a lead screw, a coupling, or any combination thereof. In some embodiments, the wireless communication device comprises a Wi-Fi sensor, a Bluetooth sensor, an RFID sensor, or any combination thereof. In some embodiments, the wireless signal comprises a medication name, a medical ailment, a medication dosage, a medication period, a medication interval, a doctor name, a patient name, a prescription date, a prescription number, a prescription barcode, a refill date, a number of refills, a pill size, a pill color, or any combination thereof. In some embodiments, the platform further comprises a security input configured to receive a security data. In some embodiments, the communication module is further configured to receive the security data from the security input. In some embodiments, the command module is further configured to command the actuator in response to the security data. In some embodiments, the security input comprises a keyhole, a button, a fingerprint scanner, a biometric scanner, a retinal scanner, a microphone, a GPS sensor, a Wi-Fi sensor, a Bluetooth sensor, an RFID sensor, a NFC sensor, or any combination thereof. In some embodiments, the memory is configured to store the input signal. In some embodiments, at least one of the smart cabinet security device and the digital processing device comprising further comprise an energy storage device. In some embodiments, the energy storage device is replaceable, rechargeable or both. In some embodiments, at least one of the smart cabinet security device and the digital processing device further comprise a charging port. In some embodiments, at least one of the smart cabinet security device and the digital processing device further comprise an indicator. In some embodiments, the indicator comprises a light, a screen, a reel, a knob, a dial, a gauge, a speaker, a screen, or any combination thereof. In some embodiments, the command module is further configured to initiate the indicator in response to at least the wireless signal. In some embodiments, at least one of the smart cabinet security device and the digital processing device further comprise at least one of a programing button and a power button. In some embodiments, the communication module configured to receive a signal from of at least one of the programming button and the power button. In some embodiments, at least one of the smart cabinet security device and the digital processing device further comprise a display screen. In some embodiments, the command module is further configured to transmit a display data to the display screen. In some embodiments, the user medical information comprises at least one of a user name, a medication name, a medical ailment, a medication dosage, a medication period, a medication interval, a doctor name, a prescription date, a pill size, and a pill color, and a patient voice pattern. In some embodiments, the communication module is further configured to transmit a dosing data based at least on the command. In some embodiments, the transmission module is further configured to receive the dosing data. In some embodiments, at least one of the memory and the storage module is configured to store the dosing data. In some embodiments, the mobile application further comprises a medication ordering module configured to order a medicament in response to at least the dosing data. In some embodiments, the transmission module is further configured to transmit a dosing alert. In some embodiments, the communication module is further configured to receive the dosing alert.

Another aspect is a child-proof smart medicament container or container cap for use with a medicament such as *Cannabis* or a *Cannabis* product. The container or container cap is preferably senior-friendly and compliant with government regulations.

Another aspect is a smart container cap that can mate with standard plastic pill bottles.

Another aspect is a smart medicament container for securing and storing a *Cannabis* product. The container can prevent theft, prevent/deter overconsumption, maintain a record of use/consumption and prevent access by others including children.

Another aspect is a medicament container for securing and storing a *Cannabis* product that complies with local, state and federal requirements.

In yet another aspect, the cap of the medicament container is linked wirelessly to a smart phone. Another aspect is a locking bottle with a cap that locks with a combination, a keyhole, a button, a fingerprint scanner, a biometric scanner, a retinal scanner, a camera, a microphone, a GPS sensor, a Wi-Fi sensor, a Bluetooth sensor, an RFID sensor, a NFC sensor, or any combination thereof.

Another aspect is an application or "App" that allows a smart phone to be used with a container such as a medicament container. A user can access the App for records related to medicament consumption including use of the medicament contact and/or container cap. The smart phone can have internet connectivity to link it to the cloud, other health applications, retail services and NFC transponders.

Also provided herein is a system comprising: a security input configured to receive a security data; a digital processing device connected to the housing, wherein the digital processing device is configured to receive the security data from a security input and to command the actuator in response to at least the security data; a medicine bottle comprising a sleeve engagement appendage; and a smart medicament container cap comprising: a housing comprising a bottle engagement coupling configured to engage with the sleeve engagement appendage; an actuator connected to the housing; and a compression plate connected to the actuator and engaged with the housing by a slideable coupling; wherein the bottle engagement coupling, the actuator, and the compression plate are configured to temporarily prevent access to contents within the medicine bottle, the medicine bottle sleeve, or both

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION OF THE INVENTION

Smart Medicament Container Cap

Figure 1:
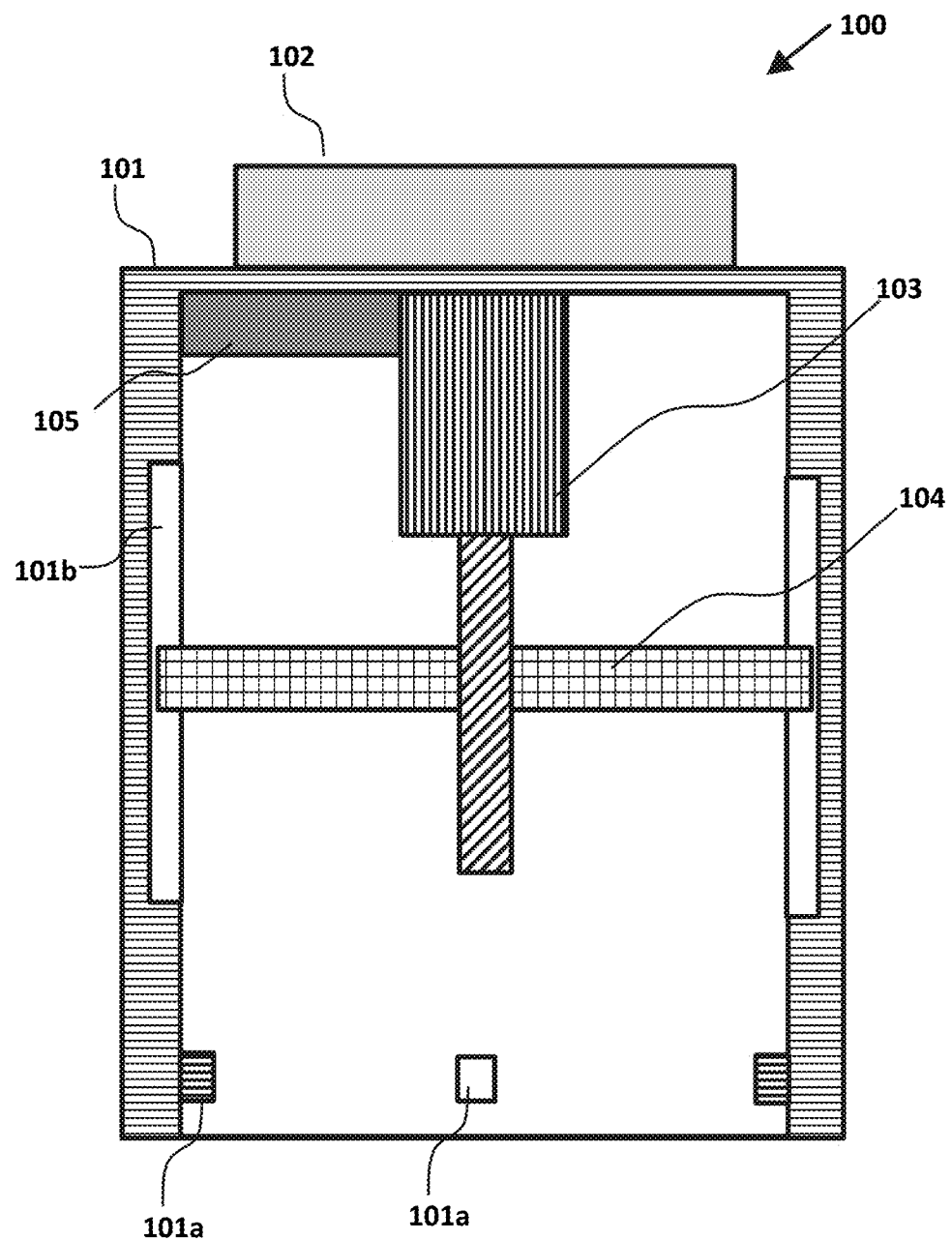
FIG. 1 shows a non-limiting example of a front cross-sectional view of a smart medicament container cap.

Provided herein, per FIGS. 1-6, is a smart medicament container cap 100 comprising a housing 101, a security input 102 connected to the housing 101, an actuator 103 connected to the housing 101, a compression plate 104 connected to the actuator 103 and a digital processing device 105 connected to the housing 101.

In some embodiments, the housing 101 comprises a bottle engagement coupling 101a configured to engage with a medicine bottle 200, a medicine bottle sleeve 600, or both.

In some embodiments, the security input 102 is configured to receive a security data. In some embodiments, the compression plate 104 is engaged with the housing 101 by a slideable coupling 101b. In some embodiments, the digital processing device 105 comprises a digital processing device. In some embodiments, the digital processing device is configured to receive the security data from a security input 102 and to command the actuator 103 in response to at least the security data.

In some embodiments, the bottle engagement coupling 101a, the actuator 103, and the compression plate 104 are configured to temporarily prevent access to contents within the medicine bottle 200, the medicine bottle sleeve 600, or both.

In some embodiments, the housing 101 comprises a first cavity having an interior housing surface and an exterior housing surface. In some embodiments, per FIGS. 1 and 2, the interior housing surface comprises the bottle engagement coupling 101a. In some embodiments, the exterior housing surface comprises the bottle engagement coupling 101a. In some embodiments, the bottle engagement coupling 101a comprises a plurality of bottle engagement couplings 101a comprising 1 to 10 bottle engagement couplings 101a. In some embodiments, the plurality of bottle engagement couplings 101a comprises a radial array of bottle engagement couplings 101a.

Figure 2:
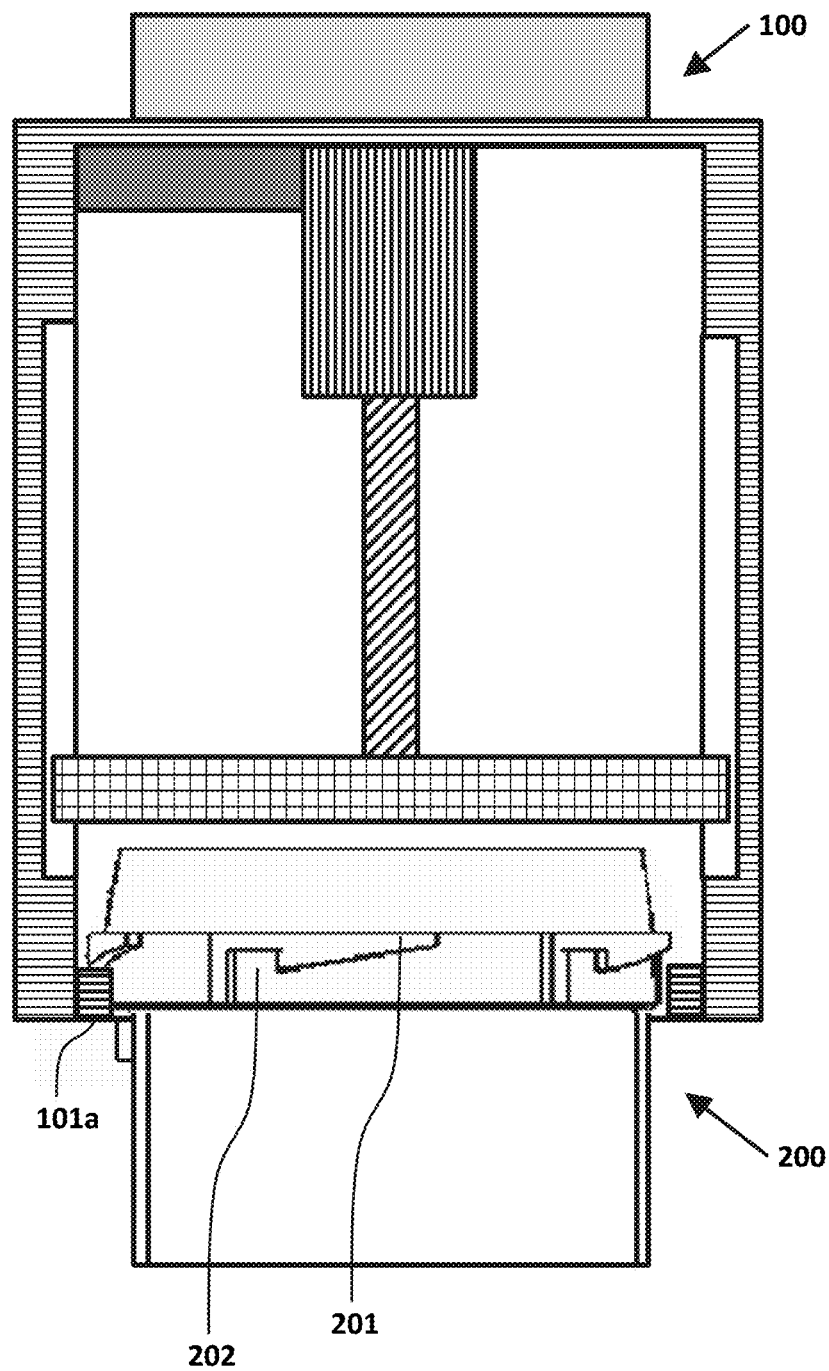
FIG. 2 shows a non-limiting example of a front cross-sectional view of a smart medicament container cap on a standard medicine bottle.

FIG. 2 shows a front cross sectional view of an exemplary non-limiting cap 100 comprising a housing 101 having a bottle engagement coupling 101a. In some embodiments, an interior housing surface of the housing 101 comprises the bottle engagement coupling 101a. In some embodiments, the interior housing surface of the housing 101 comprises a plurality of bottle engagement coupling 101a. In some embodiments, the interior housing surface of the housing 101 comprises a radial array of the plurality of bottle engagement couplings 101a. In some embodiments, the bottle engagement couplings 101a are configured to fasten the cap 100 to a standard medicine bottle 200. In some embodiments, the bottle engagement couplings 101a are configured to fasten the cap 100 to a standard medicine bottle 200 comprising a push-to-lock medicine bottle having a medicine bottle locking feature 201 comprising a radial array of a plurality of recesses 202. In some embodiments, the bottle engagement coupling 101a has a size and shape configured to fit within the recesses 202. In some embodiments, the radial array of the bottle engagement couplings 101a on the interior housing surface of the housing 101 are configured to align with the radial array of the plurality of the recesses 202.

Figure 6:
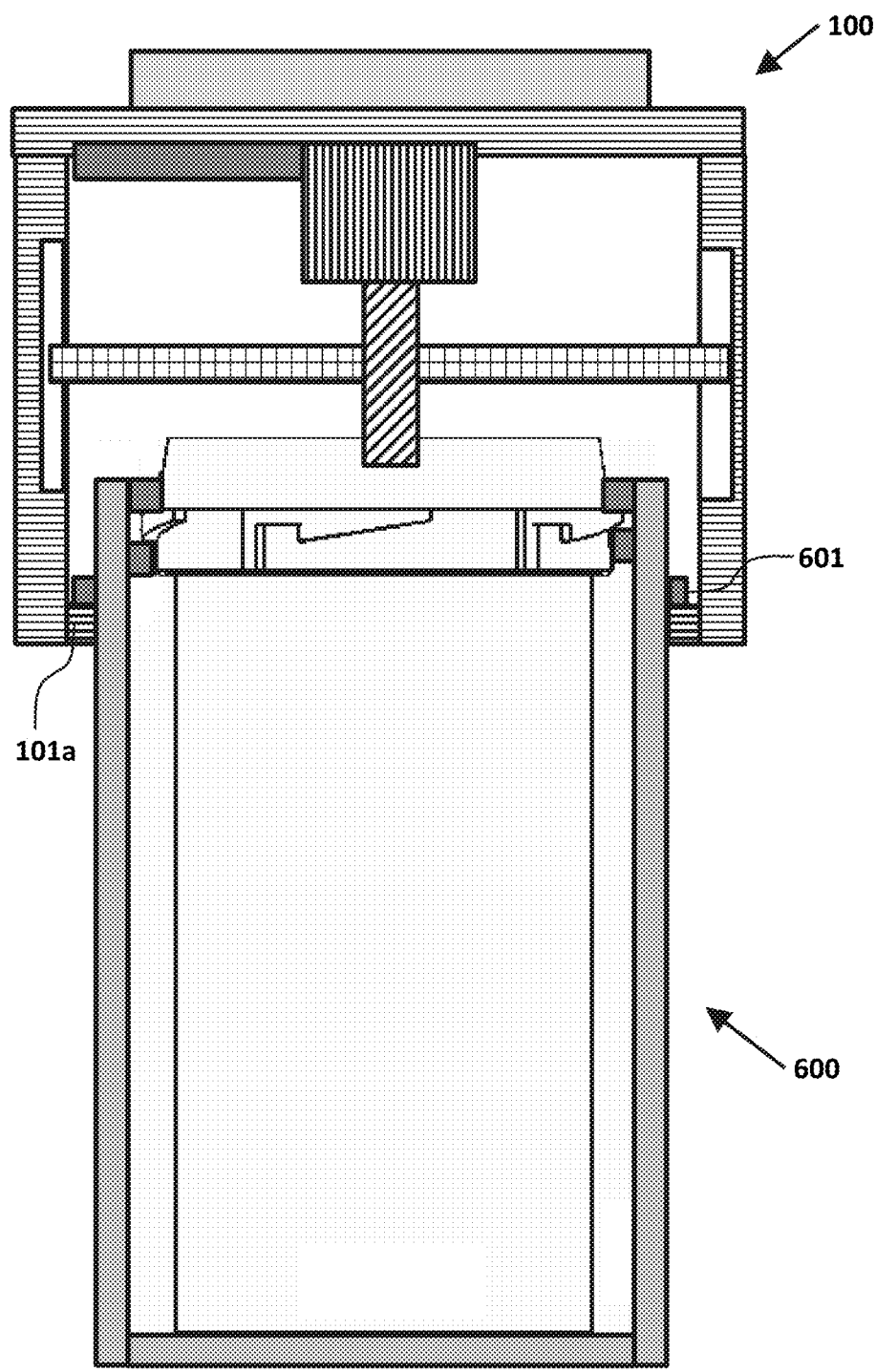
FIG. 6 shows a non-limiting example of a front cross sectional view of a smart medicament container cap, a sleeve, and a standard medicine bottle.

In some embodiments, per FIG. 6, the bottle engagement couplings 101a are configured to fasten the cap 100 to a medicine bottle sleeve 600. In some embodiments, the bottle engagement couplings 101a are configured to fasten the cap 100 to a medicine bottle sleeve 600 comprising a sleeve engagement appendage 601. In some embodiments, the sleeve engagement appendage 601 has a size and shape configured to couple with the bottle engagement coupling 101a, the plurality of recesses, or both. In some embodiments, the sleeve engagement appendage 601 comprises a radial array of a plurality of the sleeve engagement appendages 601, wherein the bottle engagement couplings 101a on the interior housing surface of the housing are configured to align with a radial array of the plurality of the sleeve engagement appendages 601.

In some embodiments, the compression plate 104 is configured to seal against an upper surface of the standard medicine bottle 200, an upper surface of the medicine bottle sleeve 600, or both. In some embodiments, the compression plate 104 is configured to form an air-tight seal against an upper surface of the standard medicine bottle 200, an upper surface of the medicine bottle sleeve 600, or both. In some embodiments, the compression plate 104 is configured to form a water-tight seal against an upper surface of the standard medicine bottle 200, an upper surface of the medicine bottle sleeve 600, or both. In some embodiments, the compression plate 104 is configured to form a seal against an upper surface of the standard medicine bottle 200, an upper surface of the medicine bottle sleeve 600, or both to temporarily prevent access to contents within the medicine bottle 200. In some embodiments, the compression plate 104 is configured to seal against an upper surface of the standard medicine bottle 200, an upper surface of the medicine bottle sleeve 600, or both, such that the seal cannot be broken by hand. In some embodiments, the compression plate 104 is configured to seal against an upper surface of the standard medicine bottle 200, an upper surface of the medicine bottle sleeve 600, or both, such that breaking the seal without initiating the actuator would damage at least one of the cap, the standard medicine bottle 200, and the medicine bottle sleeve 600.

Figure 4A:
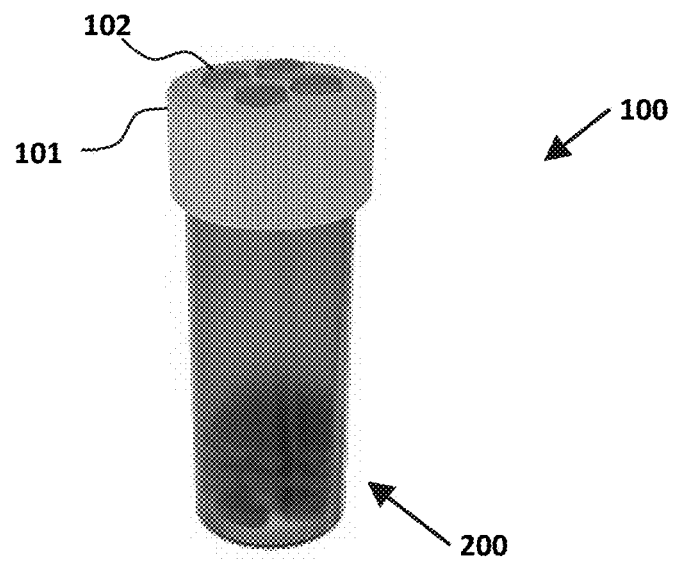
FIG. 4A shows a non-limiting example of a perspective view of a smart medicament container cap with a first security input.
Figure 4B:
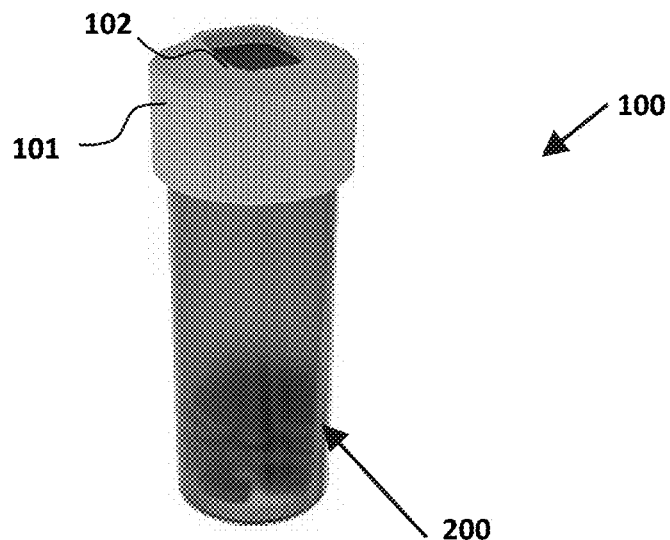
FIG. 4B shows a non-limiting example of a perspective view of a smart medicament container cap with a second security input.

In some embodiments, per FIGS. 4A-4B, the security input 102 comprises a keyhole, a button, a fingerprint scanner, a biometric scanner, a retinal scanner, a camera, a microphone, a GPS sensor, a Wi-Fi sensor, a Bluetooth sensor, an RFID sensor, a NFC sensor, or any combination thereof. In some embodiments, per FIG. 4A, the security input 102 comprises a plurality of buttons, wherein the security data comprises a combination of the buttons. In some embodiments, each of buttons comprises a unique identifier comprising a number, a letter, a symbol, or any combination thereof. In some embodiments, per FIG. 4B, the security input 102 comprises a fingerprint scanner.

Figure 3A:
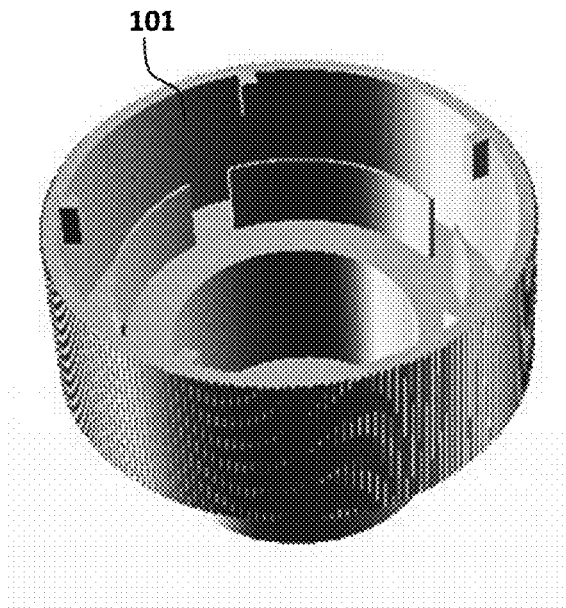
FIG. 3A shows a non-limiting example of a bottom perspective view of a first exemplary housing of the smart medicament container cap.
Figure 3B:
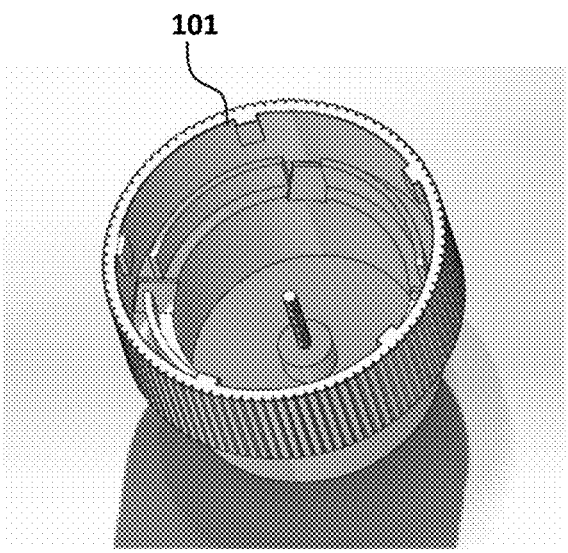
FIG. 3B shows a non-limiting example of a bottom perspective view of a second exemplary housing of the smart medicament container cap.
Figure 3C:
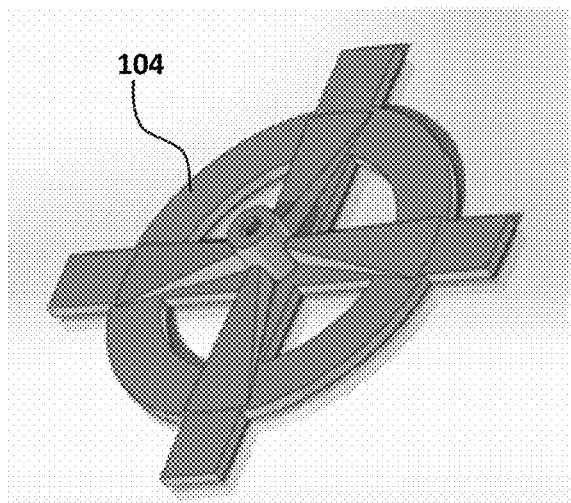
FIG. 3C shows a non-limiting example of a bottom perspective view of a first compression plate of the smart medicament container cap.
Figure 3D:
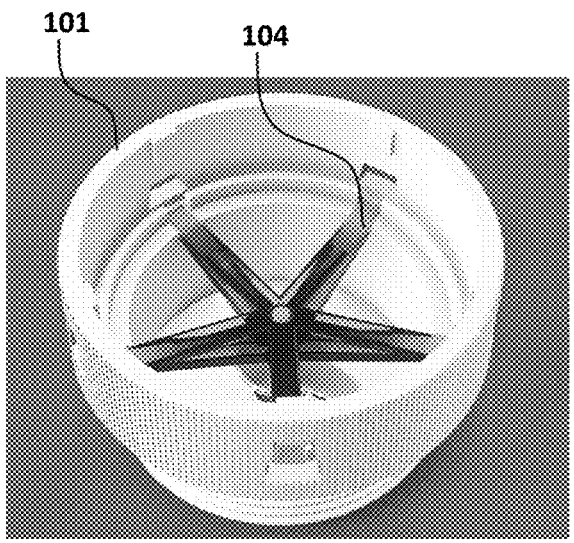
FIG. 3D shows a non-limiting example of a bottom perspective view of a second compression plate in a third exemplary housing of the smart medicament container cap.

FIGS. 3A, 3B, and 3D show exemplary housing 101 configurations of the smart medicament container cap 100. FIGS. 3C, and 3D show an exemplary first housing 101a and an exemplary second housing 101b, and an exemplary third housing 101c of the smart medicament container cap 100. In some embodiments, the slideable coupling 101b between the compression plate 104 and the housing 101 comprises a tongue, a groove, a bearing, a gear, a pulley, a slot, or any combination thereof. In some embodiments, per FIGS. 1 and 3A-3D, the slideable coupling 101b between the compression plate 104 and the housing 101 comprises a tongue within the compression plate 104 and a groove within the housing 101. In some embodiments, the slideable coupling 101b between the compression plate 104 and the housing 101 comprises a plurality of tongues within the compression plate 104 and a plurality of grooves within the housing 101. In some embodiments, the slideable coupling 101b between the compression plate 104 and the housing 101 comprises a radial array of a plurality of tongues within the compression plate 104 and a radial array of a plurality of grooves within the housing 101.

In some embodiments, the actuator 103 comprises a motor, a servomotor, a linear actuator, a solenoid, a gear, a sprocket, a nut, a belt, a chain, a bearing, a spring, a shaft, a lead screw, a coupling, or any combination thereof. In some embodiments, per FIG. 3D, the actuator comprises a lead screw and a nut, wherein the slideable coupling between the compression plate 104 and the housing 101 comprises a radial array of a plurality of tongues within the compression plate 104 and a radial array of a plurality of grooves within the housing 101, and wherein the nut is rigidly connected to the compression plate 104 to convert a rotation motion of the lead screw to a linear translation of the nut and the compression plate 104. In some embodiments, the nut and the lead screw comprise a right handed threading or a left handed threading.

In some embodiments, the connection between the housing 101 and at least one of the security input 102, the actuator 103, and the digital processing device 105 comprises a rigid connection.

In some embodiments, the digital processing device 105 further comprises a wireless communication device configured to receive a wireless signal and transmit a communications signal to the digital processing device, and wherein the communication signal is based on the wireless signal. In some embodiments, the wireless communication device comprises a Wi-Fi sensor, a Bluetooth sensor, an RFID sensor, an NFC sensor, or any combination thereof. In some embodiments, the wireless signal comprises a medication name, a medical ailment, a medication dosage, a medication period, a medication interval, a doctor name, a patient name, a prescription date, a prescription number, a prescription barcode, a refill date, a number of refills, a pill size, a pill color, or any combination thereof.

In some embodiments, the cap 100 further comprises a memory connected to the housing 101. In some embodiments, the memory is configured to store at least the wireless signal. In some embodiments, the memory is configured to store a usage data, wherein the usage data comprises at least a time and date the command. In some embodiments, the communications signal further comprises the usage data. In some embodiments, the cap 100 further comprises an energy storage device connected to the housing 101. In some embodiments, the energy storage device is replaceable, rechargeable or both. In some embodiments, the cap 100 further comprises a charging port connected to the energy storage device.

In some embodiments, the cap 100 further comprises an indicator connected to the housing 101. In some embodiments, the indicator comprises a light, a screen, a reel, a knob, a dial, a gauge, a speaker, a screen, or any combination thereof. In some embodiments, the digital processing device is further configured to initiate the indicator in response to at least the security data. In some embodiments, the cap 100 further comprises at least one of a programing button and a power button. In some embodiments, the digital processing device is further configured to detect initiation of at least the programming button and the power button. In some embodiments, the cap 100 further comprises a display screen. In some embodiments, the display screen is connected to the housing. In some embodiments, the digital processing device is further configured to transmit a display data to the display screen. In some embodiments, the cap 100 further comprises a label. In some embodiments, the cap 100 further comprises an environmental sensor comprising a thermometer, an accelerometer, a barometer, a magnetic sensor, or any combination thereof.

Medicine Bottle Sleeve

Provided herein, per FIG. 6, is a medicine bottle sleeve 600 configured to couple with a smart medicament container cap comprising a housing, an actuator connected to the housing, a compression plate connected to the actuator. In some embodiments, the medicine bottle sleeve 600 comprises at least one of a security input, a digital processing device, and a display.

In some embodiments, the medicine bottle sleeve 600 comprises a sleeve engagement appendage 601 configured to engage with the bottle engagement coupling 101a of the cap 100. In some embodiments, the sleeve engagement appendage 601 has a size and shape configured to couple with the bottle engagement coupling 601. In some embodiments, the sleeve engagement appendage 601 comprises a radial array of a plurality of the sleeve engagement appendages 601, configured to align with a radial array of the plurality of the bottle engagement couplings 101a.

In some embodiments, the bottle engagement coupling 101a, the actuator 103, and the compression plate 104 are configured to temporarily prevent access to contents within the medicine bottle sleeve 600.

In some embodiments, the medicine bottle sleeve 600 comprises a bottle containment cavity comprising an interior sleeve surface and an exterior sleeve surface. In some embodiments, the bottle containment cavity has an inner diameter configured to surround at least a portion of the medicine bottle. In some embodiments, the medicine bottle sleeve 600 has an inner diameter greater than an outer diameter of a standard medicine bottle 200. In some embodiments, the medicine bottle sleeve 600 has an inner height lesser than an outer height of a standard medicine bottle 200. In some embodiments, the medicine bottle sleeve 600 comprises a base configured to accept a standard medicine bottle 200. In some embodiments, the medicine bottle sleeve 600 further comprises an environmental sensor comprising a thermometer, an accelerometer, a barometer, a magnetic sensor, or any combination thereof.

Figures 5A, 5B:
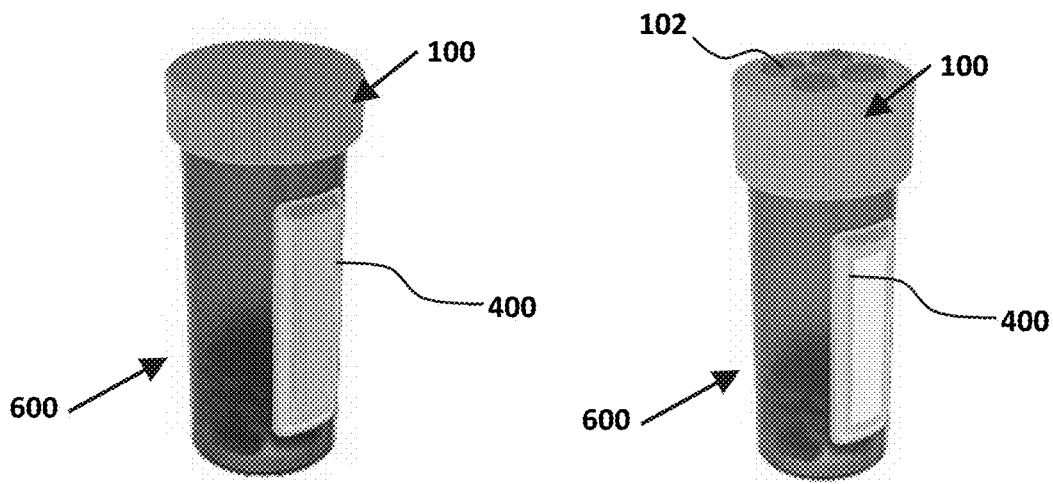
FIG. 5A shows a non-limiting example of a perspective view of a smart medicament container cap with an indicator.
FIG. 5B shows a non-limiting example of a perspective view of a smart medicament container cap with an indicator and the first security input.
Figure 5C:
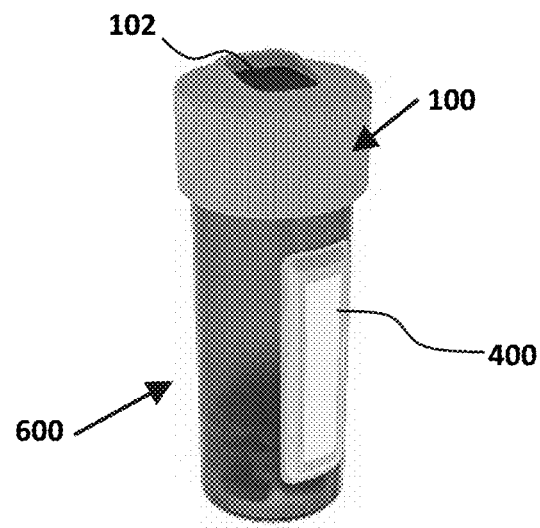
FIG. 5C shows a non-limiting example of a perspective view of a smart medicament container cap with an indicator and the second security input.

In some embodiments, per FIGS. 5A-5C, the medicine bottle sleeve 600 further comprises an indicator 400. In some embodiments, the indicator comprises a light, a screen, a reel, a knob, a dial, a gauge, a speaker, a screen, or any combination thereof. In some embodiments, the digital processing device is further configured to initiate the indicator in response to at least the security data.

In some embodiments, the medicine bottle sleeve further comprises at least one of a programing button and a power button. In some embodiments, the digital processing device is further configured to detect initiation of at least the programming button and the power button. In some embodiments, the medicine bottle sleeve further comprises a display screen. In some embodiments, the display screen is connected to the housing. In some embodiments, the digital processing device is further configured to transmit a display data to the display screen. In some embodiments, the medicine bottle sleeve further comprises a label. In some embodiments, the medicine bottle sleeve further comprises an environmental sensor comprising a thermometer, an accelerometer, a barometer, a magnetic sensor, or any combination thereof.

Smart Medicament Container

Provided herein is a smart medicament container comprising the smart medicament container cap and the medicine bottle sleeve. In some embodiments, the smart medicament container comprises a housing, a security input connected to the housing, an actuator connected to the housing, a compression plate connected to the actuator, and a digital processing device connected to the housing.

In some embodiments, the housing comprises a first cavity having an interior housing surface and an exterior housing surface. In some embodiments, at least one of the interior housing surface and the exterior housing surface comprise a bottle engagement coupling configured to engage with a medicine bottle sleeve. In some embodiments, the bottle engagement coupling comprises a plurality of bottle engagement couplings. In some embodiments, the bottle engagement coupling comprises a radial array of bottle engagement couplings.

In some embodiments, the medicine bottle sleeve comprises a sleeve engagement appendage configured to engage with the bottle engagement coupling of the cap. In some embodiments, the sleeve engagement appendage has a size and shape configured to couple with the bottle engagement coupling. In some embodiments, the sleeve engagement appendage comprises a radial array of a plurality of the sleeve engagement appendages, configured to align with a radial array of the plurality of the bottle engagement couplings.

In some embodiments, the bottle engagement coupling, the actuator, and the compression plate are configured to temporarily prevent access to contents within the cap and the medicine bottle sleeve. In some embodiments, the compression plate and the cap is configured to seal against an upper surface of the medicine bottle sleeve. In some embodiments, at least two of the compression plate, the cap, and the medicine bottle sleeve are configured to form a water-tight medicine container, an air-tight medicine container, or both. In some embodiments, the cap and the medicine bottle sleeve are configured to contain a pill, a powder, a liquid, a capsule, a syringe, a cartridge, or any combination thereof.

Smart Medicament Platform

Another aspect provided herein is a platform comprising: a smart medicament container cap, a mobile processor configured to provide a mobile application comprising: a software module configured to receive a user medical information; a storage module configured to store the user medical information; a reception module configured to receive an instruction from a user; and a transmission module configured to transmit a wireless signal based at least on the instruction and the user medical information; and a digital processing device in communication with the smart medicament container cap and the mobile processor, the digital processing device comprising: at least one processor; an operating system configured to perform executable instructions; a memory; a wireless communication device; a computer program including instructions executable by the digital processing device to create an application comprising: a communication module configured to receive a wireless signal; and a command module configured to command the actuator in response to at least the wireless signal.

In some embodiments, the digital processing device is separate and distinct from at least one of the cap, the medicine bottle, and the pill sleeve. In some embodiments, the digital processing device is permanently or removably connected to the cap or the pill sleeve. In some embodiments, the digital processing device is rigidly connected to or integrated within the cap or the pill sleeve.

In some embodiments, the housing comprises a first cavity having an interior housing surface an exterior housing surface. In some embodiments, the interior housing surface comprises the bottle engagement coupling. In some embodiments, the exterior housing surface comprises the bottle engagement coupling. In some embodiments, the bottle engagement coupling comprises a plurality of bottle engagement couplings comprising 1 to 10 bottle engagement couplings. In some embodiments, the plurality of bottle engagement couplings comprises a radial array of bottle engagement couplings. In some embodiments, the medicine bottle comprises a commercial medicine bottle. In some embodiments, the commercial medicine bottle comprises a push-to-lock medicine bottle, a pill bottle, a liquid medicine bottle, a child-resistant medicine bottle, or any combination thereof.

In some embodiments, the actuator comprises a motor, a servomotor, a linear actuator, a solenoid, a gear, a sprocket, a nut, a belt, a chain, a bearing, a spring, a shaft, a lead screw, a coupling, or any combination thereof. In some embodiments, the slideable coupling comprises a tongue, a groove, a bearing, a gear, a pulley, a slot, or any combination thereof.

In some embodiments, the cap further comprises a label. In some embodiments, the wireless communication device comprises a Wi-Fi sensor, a Bluetooth sensor, an RFID sensor, or any combination thereof. In some embodiments, the wireless signal comprises a medication name, a medical ailment, a medication dosage, a medication period, a medication interval, a doctor name, a patient name, a prescription date, a prescription number, a prescription barcode, a refill date, a number of refills, a pill size, a pill color, or any combination thereof. In some embodiments, the platform further comprises a security input configured to receive a security data. In some embodiments, the communication module is further configured to receive the security data from the security input. In some embodiments, the command module is further configured to command the actuator in response to the security data. In some embodiments, the security input comprises a keyhole, a button, a fingerprint scanner, a biometric scanner, a retinal scanner, a microphone, a GPS sensor, a Wi-Fi sensor, a Bluetooth sensor, an RFID sensor, a NFC sensor, or any combination thereof. In some embodiments, the memory is configured to store the input signal. In some embodiments, the memory is configured to store a usage data, wherein the usage data comprises at least a time and date the command. In some embodiments, the communications signal further comprises the usage data.

In some embodiments, at least one of the cap and the digital processing device comprising further comprise an energy storage device. In some embodiments, the energy storage device is replaceable, rechargeable or both. In some embodiments, at least one of the cap and the digital processing device further comprise a charging port. In some embodiments, at least one of the cap and the digital processing device further comprise an indicator. In some embodiments, the indicator comprises a light, a screen, a reel, a knob, a dial, a gauge, a speaker, a screen, or any combination thereof. In some embodiments, the command module is further configured to initiate the indicator in response to at least the wireless signal. In some embodiments, at least one of the cap and the digital processing device further comprise at least one of a programing button and a power button. In some embodiments, the communication module configured to receive a signal from of at least one of the programming button and the power button. In some embodiments, at least one of the cap and the digital processing device further comprise a display screen. In some embodiments, the command module is further configured to transmit a display data to the display screen.

In some embodiments, the user medical information comprises at least one of a user name, a medication name, a medical ailment, a medication dosage, a medication period, a medication interval, a doctor name, a prescription date, a pill size, and a pill color, and a patient voice pattern. In some embodiments, the communication module is further configured to transmit a dosing data based at least on the command. In some embodiments, the transmission module is further configured to receive the dosing data. In some embodiments, at least one of the memory and the storage module is configured to store the dosing data. In some embodiments, the mobile application further comprises a medication ordering module configured to order a medicament in response to at least the dosing data. In some embodiments, the transmission module is further configured to transmit a dosing alert. In some embodiments, the communication module is further configured to receive the dosing alert.

In some embodiments, the platform comprises two or more caps, wherein each cap is associated with different user medical information. In some embodiments, the platform further comprises the medicine bottle sleeve. In some embodiments, the medicine bottle sleeve comprises a bottle containment cavity comprising an interior sleeve surface and an exterior sleeve surface. In some embodiments, the bottle containment cavity has an inner diameter configured to surround at least a portion of the medicine bottle.

In some embodiments, the medicine bottle comprises a commercial medicine bottle. In some embodiments, the commercial medicine bottle comprises a push-to-lock medicine bottle, a pill bottle, a liquid medicine bottle, a child-resistant medicine bottle, or any combination thereof. In some embodiments, the medicine bottle sleeve comprises a sleeve engagement appendage configured to engage with the bottle engagement coupling.

In some embodiments, the interior housing surface comprises the sleeve engagement appendage. In some embodiments, the exterior housing surface comprises the sleeve engagement appendage. In some embodiments, the sleeve engagement appendage comprises 1 to 10 sleeve engagement appendages. In some embodiments, the sleeve engagement appendage comprises a radial array of sleeve engagement appendages.

Smart Medicament System

Another aspect provided herein is a system comprising: a security input configured to receive a security data; a digital processing device connected to the housing, wherein the digital processing device is configured to receive the security data from a security input and to command the actuator in response to at least the security data; a medicine bottle sleeve comprising a sleeve engagement appendage; and a smart medicament container cap.

In some embodiments, the cap comprises housing comprising a bottle engagement coupling configured to engage with a sleeve engagement appendage, an actuator connected to the housing, and a compression plate connected to the actuator and engaged with the housing by a slideable coupling. In some embodiments, wherein the bottle engagement coupling, the actuator, and the compression plate are configured to temporarily prevent access to contents within the medicine bottle, the medicine bottle sleeve, or both.

In some embodiments, at least one of the digital processing device and the security input are separate and distinct from at least one of the cap and the pill sleeve. In some embodiments, at least one of the digital processing device and the security input are permanently or removably connected the cap or the pill sleeve. In some embodiments, at least one of the digital processing device and the security input are rigidly connected to or integrated within the cap or the pill sleeve.

In some embodiments, the housing comprises a cavity having an interior housing surface and an exterior housing surface. In some embodiments, the interior housing surface comprises the bottle engagement coupling. In some embodiments, the exterior housing surface comprises the bottle engagement coupling. In some embodiments, the bottle engagement coupling comprises a plurality of bottle engagement couplings comprising 1 to 10 bottle engagement couplings. In some embodiments, the plurality of bottle engagement couplings comprises a radial array of bottle engagement couplings. In some embodiments, the medicine bottle sleeve comprises a bottle containment cavity having an interior sleeve surface and an exterior sleeve surface. In some embodiments, the bottle containment cavity has an inner diameter configured to surround at least a portion of a medicine bottle. In some embodiments, the medicine bottle comprises commercial medicine bottle comprising a push-to-lock medicine bottle, a pill bottle, a liquid medicine bottle, a child-resistant medicine bottle, or any combination thereof. In some embodiments, the interior sleeve surface comprises the sleeve engagement appendage. In some embodiments, the exterior sleeve surface comprises the sleeve engagement recess. In some embodiments, the sleeve engagement recess comprises 1 to 10 sleeve engagement appendages. In some embodiments, the sleeve engagement recess comprises a radial array of sleeve engagement appendages.

In some embodiments, the security input comprises a keyhole, a button, a fingerprint scanner, a biometric scanner, a retinal scanner, a camera, a microphone, a GPS sensor, a Wi-Fi sensor, a Bluetooth sensor, an RFID sensor, a NFC sensor, or any combination thereof. In some embodiments, the actuator comprises a motor, a servomotor, a linear actuator, a solenoid, a gear, a sprocket, a nut, a belt, a chain, a bearing, a spring, a shaft, a lead screw, a coupling, or any combination thereof. In some embodiments, the slideable coupling between the compression plate and the housing comprises a tongue, a groove, a bearing, a gear, a pulley, a slot, or any combination thereof. In some embodiments, the digital processing device further comprises a wireless communication device configured to receive a wireless signal. In some embodiments, the wireless communication device comprises a Wi-Fi sensor, a Bluetooth sensor, an RFID sensor, an NFC sensor, or any combination thereof. In some embodiments, the wireless signal comprises a medication name, a medical ailment, a medication dosage, a medication period, a medication interval, a doctor name, a patient name, a prescription date, a prescription number, a prescription barcode, a refill date, a number of refills, a pill size, a pill color, or any combination thereof. In some embodiments, the system further comprises a memory. In some embodiments, the memory is configured to store at least the wireless signal. In some embodiments, the memory is permanently or removably connected the cap or the pill sleeve. In some embodiments, the memory is rigidly connected to or integrated within the cap or the pill sleeve.

In some embodiments, the system further comprises an energy storage device. In some embodiments, the energy storage device is permanently or removably connected the cap or the pill sleeve. In some embodiments, the energy storage device is rigidly connected to or integrated within the cap or the pill sleeve. In some embodiments, the system further comprises an energy storage device. In some embodiments, the energy storage device is replaceable, rechargeable or both. In some embodiments, the system further comprises a charging port connected to the energy storage device. In some embodiments, the system further comprises an indicator rigidly connected to or integrated within the cap or the pill sleeve. In some embodiments, the indicator comprises a light, a screen, a reel, a knob, a dial, a gauge, a speaker, a screen, or any combination thereof.

In some embodiments, the digital processing device is further configured to initiate the indicator in response to at least the security data. In some embodiments, the system further comprises at least one of a programing button and a power button. In some embodiments, at least one of a programing button and a power button are rigidly connected to or integrated within the cap or the pill sleeve. In some embodiments, the digital processing device is further configured to detect initiation of at least the programming button and the power button. In some embodiments, the system further comprises a display screen. In some embodiments, the display screen is rigidly connected to or integrated within the cap or the pill sleeve. In some embodiments, the digital processing device is further configured to transmit a display data to the display screen. In some embodiments, the at least one of the cap and the sleeve further comprise a label.

Medicine Cabinet System

Figure 7A:
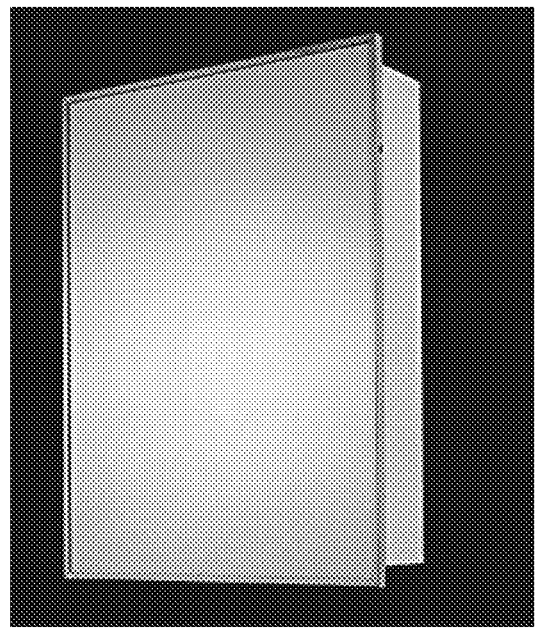
FIG. 7A shows a front view of a prior art medicine cabinet.
Figure 7B:
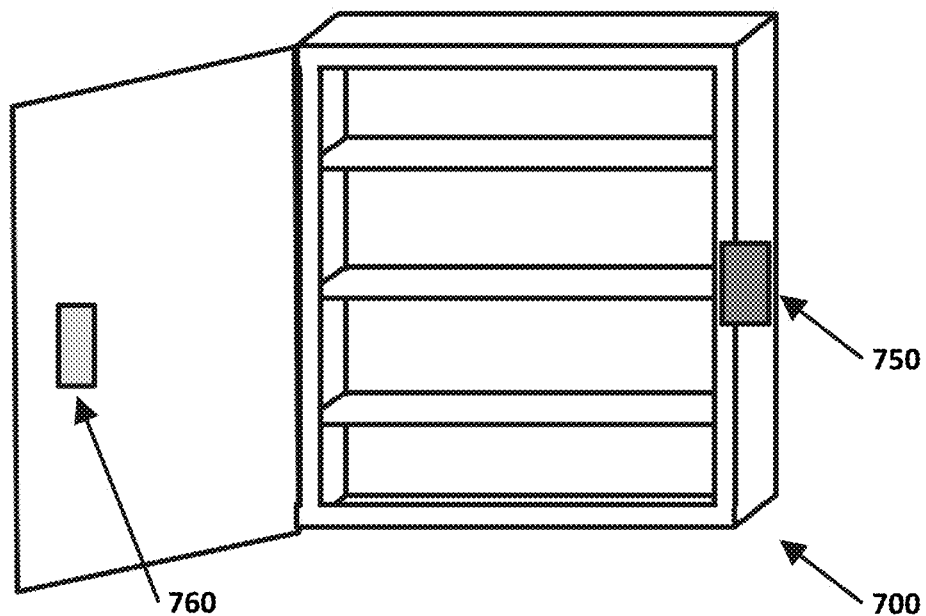
FIG. 7B shows a non-limiting example of a cabinet and a smart cabinet security device.

Another aspect provided herein, per FIG. 7B, is a system comprising a medicine cabinet 700 and a smart cabinet security device 750 comprising a housing comprising a cabinet engagement coupling configured to engage with the medicine cabinet; and an electromagnetic actuator connected to the housing, a mobile processor configured to provide a mobile application comprising: a software module configured to receive a user medical information; a storage module configured to store the user medical information; a reception module configured to receive an instruction from a user; and a transmission module configured to transmit a wireless signal based at least on the instruction and the user medical information; and a digital processing device in communication with the smart cabinet security device and the mobile processor, the digital processing device comprising: at least one processor; an operating system configured to perform executable instructions; a memory; a wireless communication device; and a computer program including instructions executable by the digital processing device to create an application comprising: a communication module configured to receive a wireless signal; and a command module configured to command the actuator in response to at least the wireless signal. In some embodiments, the digital processing device is separate and distinct from the smart cabinet security device.

In some embodiments, the system further comprises a catch 760, wherein the catch is configured to permanently affix to the medicine cabinet 700, and wherein the catch 760 is configured to releasably engage with the cabinet engagement coupling. In some embodiments, the catch 760 is permanently affixed to the medicine cabinet 700 without screws.

In some embodiments, the digital processing device is permanently or removably connected to the smart cabinet security device. In some embodiments, the digital processing device is rigidly connected to or integrated within the smart cabinet security device. In some embodiments, the cabinet engagement coupling comprises a plurality of cabinet engagement couplings comprising 1 to 10 cabinet engagement couplings. In some embodiments, the cabinet engagement coupling comprises at least one of an adhesive, a tape, an epoxy, a cement, a screw, a bolt, a nut, a nail, a security screw, a security seal, a band, and a tie. In some embodiments, the medicine cabinet comprises a commercial medicine cabinet. In some embodiments, the actuator comprises a motor, a servomotor, a linear actuator, a solenoid, a gear, a sprocket, a nut, a belt, a chain, a bearing, a spring, a shaft, a lead screw, a coupling, or any combination thereof.

In some embodiments, the wireless communication device comprises a Wi-Fi sensor, a Bluetooth sensor, an RFID sensor, or any combination thereof. In some embodiments, the wireless signal comprises a medication name, a medical ailment, a medication dosage, a medication period, a medication interval, a doctor name, a patient name, a prescription date, a prescription number, a prescription barcode, a refill date, a number of refills, a pill size, a pill color, or any combination thereof. In some embodiments, the system further comprises a security input configured to receive a security data. In some embodiments, the communication module is further configured to receive the security data from the security input. In some embodiments, the command module is further configured to command the actuator in response to the security data. In some embodiments, the security input comprises a keyhole, a button, a fingerprint scanner, a biometric scanner, a retinal scanner, a microphone, a GPS sensor, a Wi-Fi sensor, a Bluetooth sensor, an RFID sensor, a NFC sensor, or any combination thereof. In some embodiments, the memory is configured to store the input signal.

In some embodiments, at least one of the smart cabinet security device and the digital processing device comprising further comprise an energy storage device. In some embodiments, the energy storage device is replaceable, rechargeable or both. In some embodiments, at least one of the smart cabinet security device and the digital processing device further comprise a charging port. In some embodiments, at least one of the smart cabinet security device and the digital processing device further comprise an indicator. In some embodiments, the indicator comprises a light, a screen, a reel, a knob, a dial, a gauge, a speaker, a screen, or any combination thereof.

In some embodiments, the command module is further configured to initiate the indicator in response to at least the wireless signal. In some embodiments, at least one of the smart cabinet security device and the digital processing device further comprise at least one of a programing button and a power button. In some embodiments, the communication module configured to receive a signal from of at least one of the programming button and the power button. In some embodiments, at least one of the smart cabinet security device and the digital processing device further comprise a display screen. In some embodiments, the command module is further configured to transmit a display data to the display screen. In some embodiments, the user medical information comprises at least one of a user name, a medication name, a medical ailment, a medication dosage, a medication period, a medication interval, a doctor name, a prescription date, a pill size, and a pill color, and a patient voice pattern. In some embodiments, the communication module is further configured to transmit a dosing data based at least on the command. In some embodiments, the transmission module is further configured to receive the dosing data. In some embodiments, at least one of the memory and the storage module is configured to store the dosing data. In some embodiments, the mobile application further comprises a medication ordering module configured to order a medicament in response to at least the dosing data. In some embodiments, the transmission module is further configured to transmit a dosing alert. In some embodiments, the communication module is further configured to receive the dosing alert.

In some embodiments, the smart cabinet security device 750 is permanently affixed to the medicine cabinet 700. In some embodiments, the smart cabinet security device 750 is permanently affixed to the medicine cabinet 700 without screws. An exemplary non-limiting standard medicine cabinet 700 is shown in FIG. 7B.

Smart Medicament Application

Provided herein, per FIGS. 8-11, is a smart medicament application for protecting, identifying, locating, generating report data, reminding, analyzing, and managing prescription medication. In some embodiments, the hardware and firmware of the smart medicament application are configured for use with biometric sensors, wireless communications equipment, RFID tags, RFID readers, linear barcode readers, employed with or without a mobile smartphone.

In some embodiments, the smart medicament application can be controlled by a user, a caregiver, a custodian, a medical technician, a doctor, or any combination thereof.

In some embodiments, the application employs voice recognition to validate a user and/or respond to their command. In some embodiments, the application comprises a feature to display GPS data emitted by a GPS sensor on the smart medicament container cap or the medicine bottle sleeve, to determine the location of the device. In some embodiments, the application is configured to enable at least one of an indicator and a screen of the smart medicament container cap or the medicine bottle sleeve. In some embodiments, the application is configured to enable at least one of an indicator and a screen of the smart medicament container cap or the medicine bottle sleeve in response to a request for that specific user medical information.

In some embodiments, the application is further configured to remind the user via a text message or a push notification regarding an upcoming prescription dosing time, an upcoming refill time, or any combination thereof.

Terms and Definitions

Unless otherwise defined, all technical terms used herein have the same meaning as commonly understood by one of ordinary skill in the art to which this disclosure belongs.

As used herein, the singular forms "a," "an," and "the" include plural references unless the context clearly dictates otherwise. Any reference to "or" herein is intended to encompass "and/or" unless otherwise stated.

As used herein, the term "about" refers to an amount that is near the stated amount by 10%, 5%, or 1%, including increments therein.

The term "*Cannabis*" refers to a group of three plants with psychoactive properties, known as *Cannabis sativa*, *Cannabis indica*, and *Cannabis ruderalis*. *Cannabis* is made up of more than 120 components, which are known as cannabinoids. The main cannabinoids are cannabidiol (CBD) and tetrahydrocannabinol (THC). CBD is a psychoactive cannabinoid, that is non-intoxicating and non-euphoric. It is often used therapeutically to help reduce inflammation and pain. It can also ease nausea, migraine, seizures, and anxiety. THC is the main psychoactive compound in *Cannabis*. THC is responsible for the "high" that most people associate with *Cannabis*.

The term "adult-use" comes from the notion that not all patrons of a *Cannabis* dispensary are consuming *Cannabis* solely for recreational purposes. *Cannabis* can be consumed for reasons other than recreational and medicinal.

The term "edible," "*Cannabis* edible," or "*Cannabis*-infused food" refers to nonmedical *Cannabis* that is prepared for consumption in baked goods (e.g. cookies or brownies), candies (e.g. gummies) and beverages. Legal edibles are available in several US states and became commercially available in Canada in late 2019.

The term "medicament" refers to something that treats or prevents or alleviates the symptoms of disease. medication, medicinal drug, medicine. Common medicaments include prescription and over the counter (OTC) drugs. Medicaments can also include products that include CBD and/or THC for both therapeutic, recreational or adult use.

The term "vape" or "*Cannabis* vaporization" refers to the use of vapor to disseminate cannabinoids into the bloodstream. There are various vaping devices (e.g. dab pens) that can be used to consume *Cannabis*.

The term "smart" refers to a device that includes the intelligence and communications to enable automatic or remote control based on user preferences or external signals from a utility or third-party energy service provider. As used herein, the device can be a cap, lock, tab, sleeve, bottle or container for storage of a medicament.

Digital Processing Device

In some embodiments, the platforms, systems, media, and methods described herein include a digital processing device, or use of the same. In further embodiments, the digital processing device includes one or more hardware central processing units (CPUs) or general purpose graphics processing units (GPGPUs) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. Those of skill in the art will also recognize that suitable media streaming device operating systems include, by way of non-limiting examples, Apple TV®, Roku®, Boxee®, Google TV®, Google Chromecast®, Amazon Fire®, and Samsung® HomeSync®. Those of skill in the art will also recognize that suitable video game console operating systems include, by way of non-limiting examples, Sony® PS3®, Sony® PS4®, Microsoft® Xbox 360®, Microsoft Xbox One, Nintendo® Wii®, Nintendo® Wii U®, and Ouya®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In yet other embodiments, the display is a head-mounted display in communication with the digital processing device, such as a VR headset. In further embodiments, suitable VR headsets include, by way of non-limiting examples, HTC Vive, Oculus Rift, Samsung Gear VR, Microsoft HoloLens, Razer OSVR, FOVE VR, Zeiss VR One, Avegant Glyph, Freefly VR headset, and the like. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Figure 12:
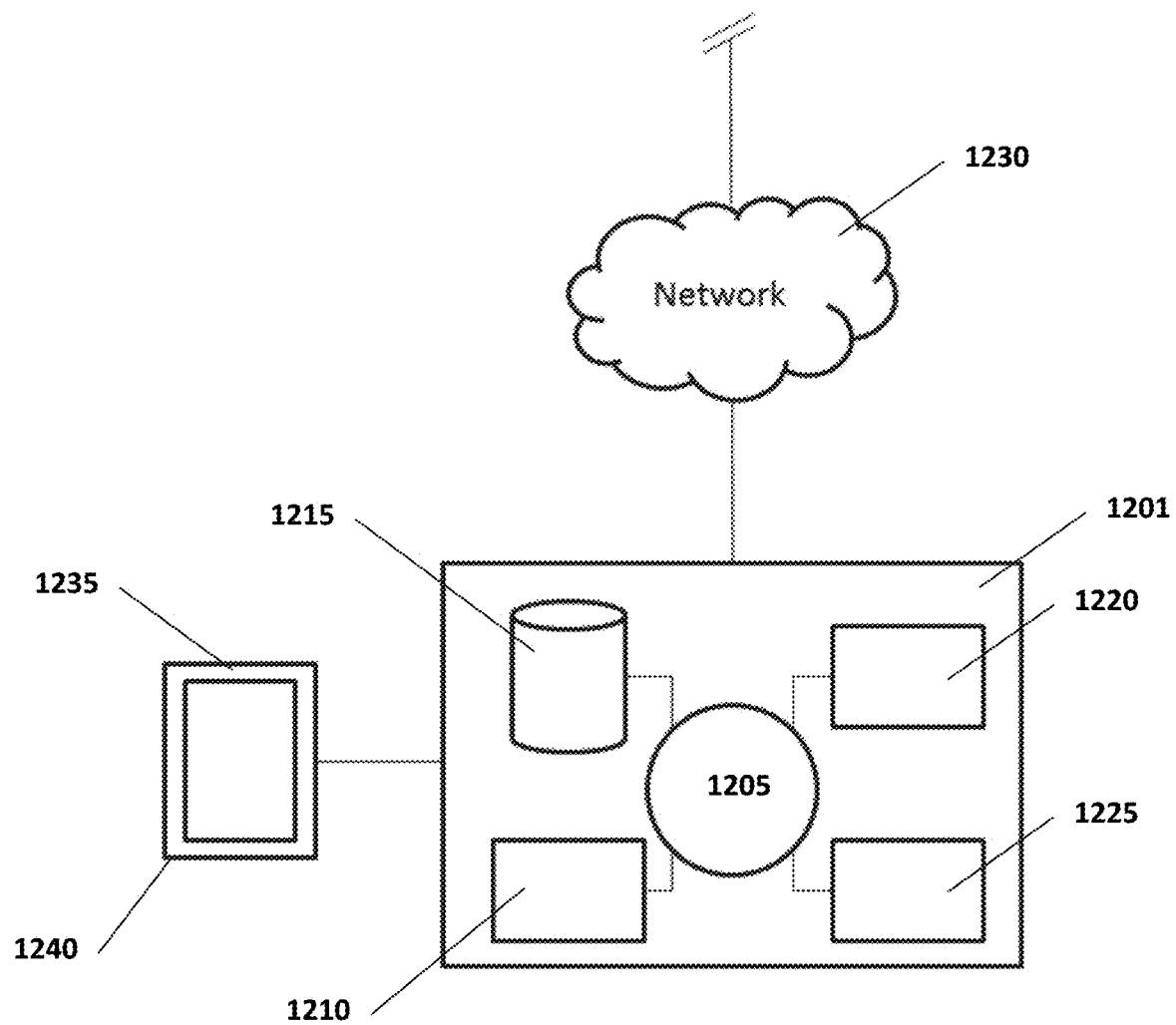
FIG. 12 shows a non-limiting example of a digital processing device; in this case, a device with one or more CPUs, a memory, a communication interface, and a display.

Referring to FIG. 12, in a particular embodiment, a digital processing device 1201 is programmed or otherwise configured to receive and send instructions based on prescription and dosing data. The device 1201 is programmed or otherwise configured to protect, identify, locate, generate reports, remind, analyze and manage a user medication and dosing. In this embodiment, the digital processing device 1201 includes a central processing unit (CPU, also "processor" and "computer processor" herein) 1205, which is optionally a single core, a multi core processor, or a plurality of processors for parallel processing. The digital processing device 1201 also includes memory or memory location 1210 (e.g., random-access memory, read-only memory, flash memory), electronic storage unit 1215 (e.g., hard disk), communication interface 1220 (e.g., network adapter) for communicating with one or more other systems, and peripheral devices 1225, such as cache, other memory, data storage and/or electronic display adapters. The memory 1210, storage unit 1215, interface 1220 and peripheral devices 1225 are in communication with the CPU 1205 through a communication bus (solid lines), such as a motherboard. The storage unit 1215 comprises a data storage unit (or data repository) for storing data. The digital processing device 1201 is optionally operatively coupled to a computer network ("network") 1230 with the aid of the communication interface 1220. The network 1230, in various cases, is the internet, an internet, and/or extranet, or an intranet and/or extranet that is in communication with the internet. The network 1230, in some cases, is a telecommunication and/or data network. The network 1230 optionally includes one or more computer servers, which enable distributed computing, such as cloud computing. The network 1230, in some cases, with the aid of the device 1201, implements a peer-to-peer network, which enables devices coupled to the device 1201 to behave as a client or a server.

Continuing to refer to FIG. 12, the CPU 1205 is configured to execute a sequence of machine-readable instructions, embodied in a program, application, and/or software. The instructions are optionally stored in a memory location, such as the memory 1210. The instructions are directed to the CPU 105, which subsequently program or otherwise configure the CPU 1205 to implement methods of the present disclosure. Examples of operations performed by the CPU 1205 include fetch, decode, execute, and write back. The CPU 1205 is, in some cases, part of a circuit, such as an integrated circuit. One or more other components of the device 1201 are optionally included in the circuit. In some cases, the circuit is an application specific integrated circuit (ASIC) or a field programmable gate array (FPGA).

Continuing to refer to FIG. 12, the storage unit 1215 optionally stores files, such as drivers, libraries and saved programs. The storage unit 1215 optionally stores user data, e.g., user preferences and user programs. The digital processing device 1201, in some cases, includes one or more additional data storage units that are external, such as located on a remote server that is in communication through an intranet or the internet.

Continuing to refer to FIG. 12, the digital processing device 1201 optionally communicates with one or more remote computer systems through the network 1230. For instance, the device 1201 optionally communicates with a remote computer system of a user. Examples of remote computer systems include personal computers (e.g., portable PC), slate or tablet PCs (e.g., Apple® iPad, Samsung® Galaxy Tab, etc.), smartphones (e.g., Apple® iPhone, Android-enabled device, Blackberry®, etc.), or personal digital assistants.

Methods as described herein are optionally implemented by way of machine (e.g., computer processor) executable code stored on an electronic storage location of the digital processing device 101, such as, for example, on the memory 1210 or electronic storage unit 1215. The machine executable or machine readable code is optionally provided in the form of software. During use, the code is executed by the processor 1205. In some cases, the code is retrieved from the storage unit 1215 and stored on the memory 1210 for ready access by the processor 1205. In some situations, the electronic storage unit 1215 is precluded, and machine-executable instructions are stored on the memory 1210.

Non-Transitory Computer Readable Storage Medium

In some embodiments, the platforms, systems, media, and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the platforms, systems, media, and methods disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Figure 13:
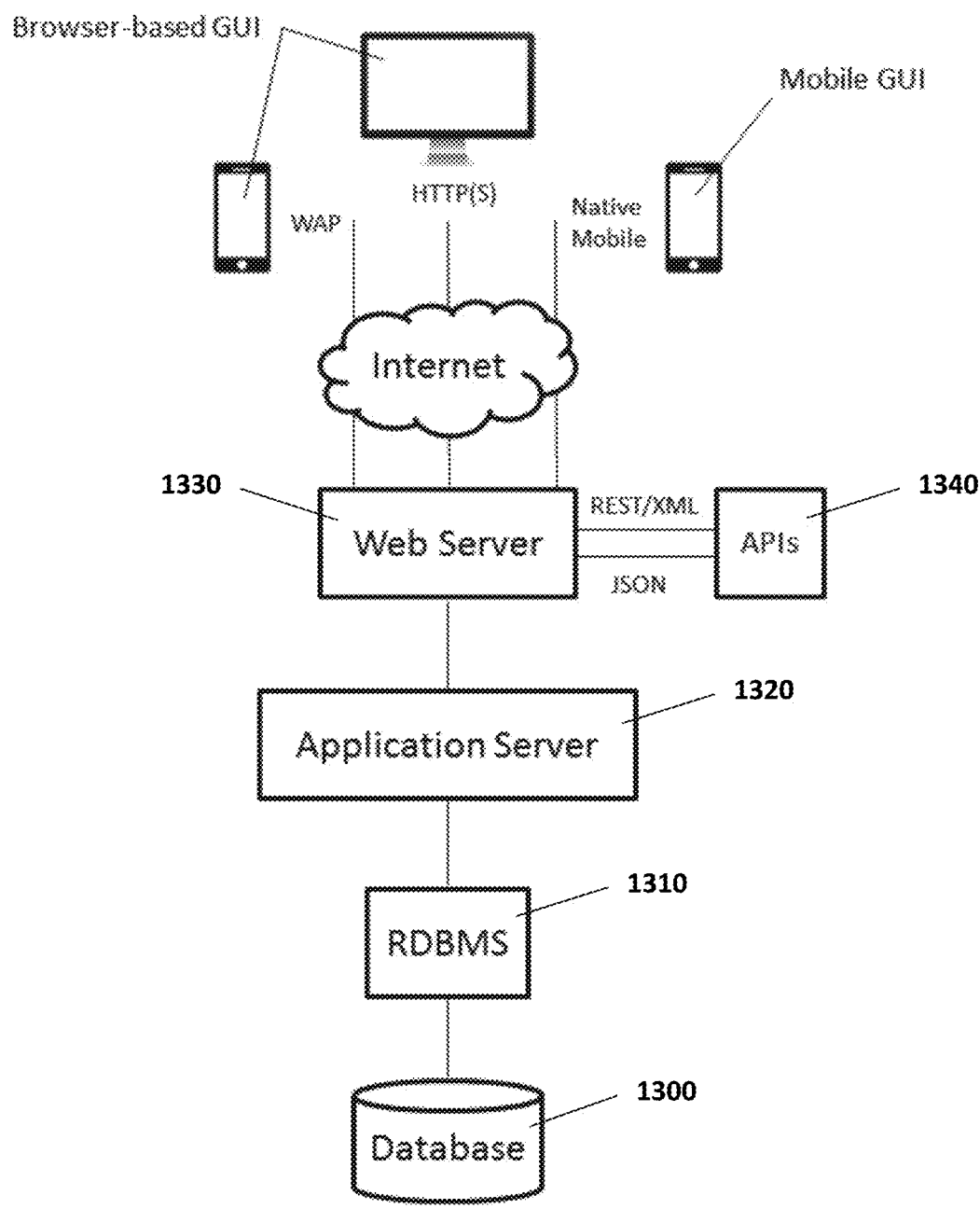
FIG. 13 shows a non-limiting example of a web/mobile application provision system; in this case, a system providing browser-based and/or native mobile user interfaces.

Referring to FIG. 13, in a particular embodiment, an application provision system comprises one or more databases 1300 accessed by a relational database management system (RDBMS) 1310. Suitable RDBMSs include Firebird, MySQL, PostgreSQL, SQLite, Oracle Database, Microsoft SQL Server, IBM DB2, IBM Informix, SAP Sybase, SAP Sybase, Teradata, and the like. In this embodiment, the application provision system further comprises one or more application severs 1320 (such as Java servers, .NET servers, PHP servers, and the like) and one or more web servers 1330 (such as Apache, IIS, GWS and the like). The web server(s) optionally expose one or more web services via app application programming interfaces (APIs) 1340. Via a network, such as the internet, the system provides browser-based and/or mobile native user interfaces.

Figure 14:
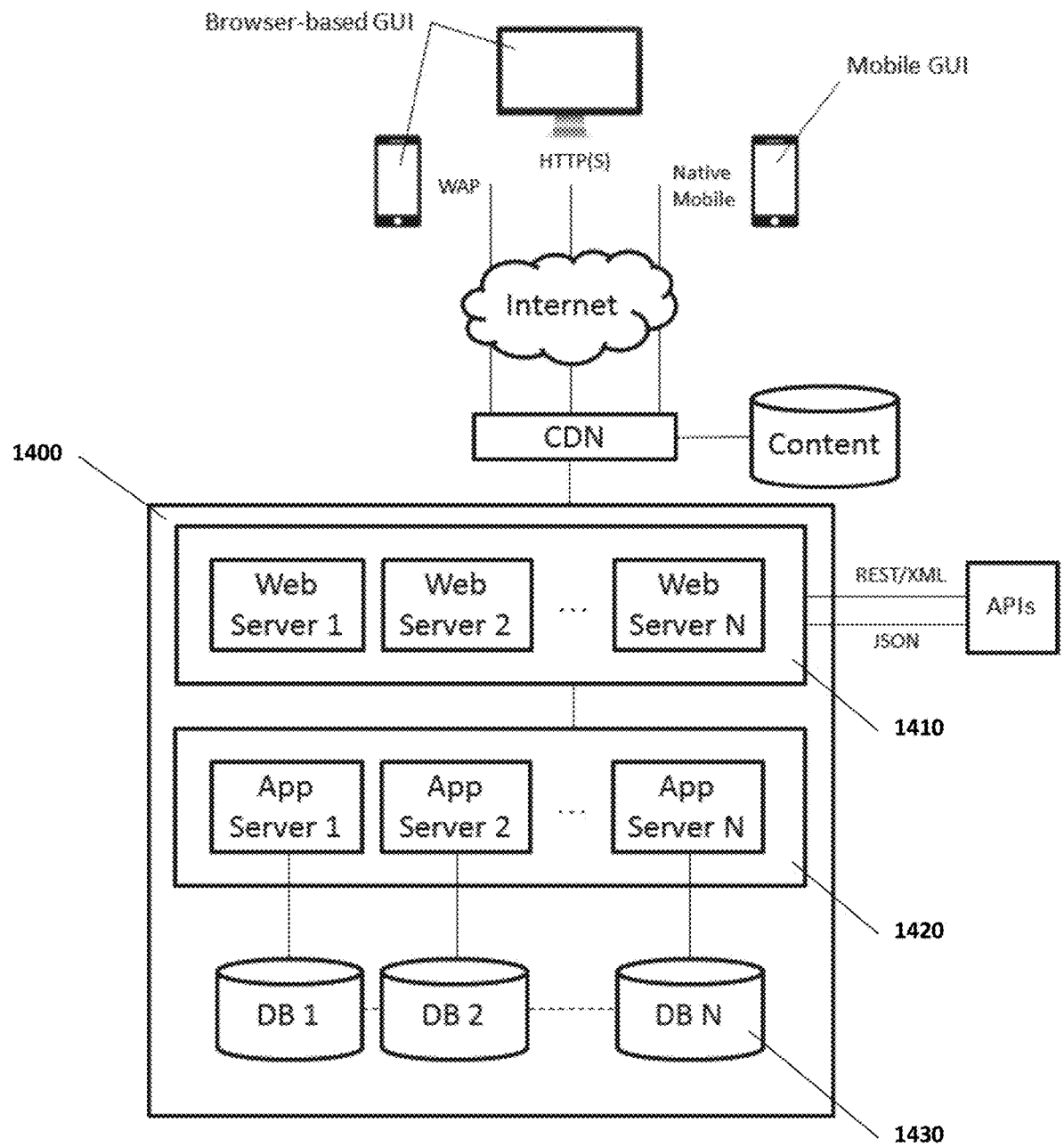
FIG. 14 shows a non-limiting example of a cloud-based web/mobile application provision system; in this case, a system comprising an elastically load balanced, auto-scaling web server and application server resources as well synchronously replicated databases

Referring to FIG. 14, in a particular embodiment, an application provision system alternatively has a distributed, cloud-based architecture 1400 and comprises elastically load balanced, auto-scaling web server resources 1410, and application server resources 1420 as well synchronously replicated databases 1430.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Google® Play, Chrome WebStore, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Web Browser Plug-In

In some embodiments, the computer program includes a web browser plug-in (e.g., extension, etc.). In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®.

In view of the disclosure provided herein, those of skill in the art will recognize that several plug-in frameworks are available that enable development of plug-ins in various programming languages, including, by way of non-limiting examples, C++, Delphi, Java™, PHP, Python™, and VB .NET, or combinations thereof.

Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called mircrobrowsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for storing and receiving updates regarding medication dosing and prescription parameters. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In other embodiments, a database is based on one or more local computer storage devices.

Non-Limiting Embodiments

Smart Caps, Locks, Tabs, Sleeves, or Base of any bottle or a similar system for other types of containers including, Cabinets Bottles or Boxes designed for storing Prescription or Non Prescription Medicine, Vitamins or Supplements Longevity Health Corp. is introducing a new type of drug packaging and logistics system for personal use and care of consumer medications, vitamins, and supplements through a series of related inventions to be known as "Vital Smart."

Further the product groups and or variations may be supported by an Artificial Intelligence, Smart Phone App, or autonomously via voice control, biometric identification, or other input of either systems or methods which supports each platform together or separately.

Vital Smart is an electronic apparatus designed for the purpose and use to protect, identify, locate, and manage medication using advanced micro electronics and communications technologies in one of several ways.

A new type of drug packaging and logistics system for personal use and care of consumer medications, vitamins and supplements through a series of related inventions to be known as "Vital Smart."

Further the product groups and or variations may be supported by an Artificial Intelligence, Smart Phone App, or autonomously of either systems or methods which supports each platform together or separately.

Vital Smart is an electronic apparatus designed for the purpose and use to protect, identify, locate, and manage medication using advanced micro electronics and communications technologies in one of several ways including:

The Vital Smart Cap, An electronic replacement cap to a standard bottle or container;

With a mechanical Locking Mechanism, (The Mechanical Locking Mechanism is achieved by one of many solutions including heat locks, electromagnetic controls and or mechanical geared slide locks) or without a mechanical locking mechanism, or an autonomous Mechanical Locking Mechanism without the standard features of the Vital Smart Cap.

The Vital Smart Tab, an electronic strip or tab having all or some of the electronic capabilities of the Vital Smart Cap however in the form of factor of a strip or tab which adheres to a standard bottle or container which may be replaceable, removed and used for a new or separate container.

The Vital Smart Sleeve, an electronic sleeve whereby a standard bottle or container can be inserted and contained having all or some of the electronic capabilities of the Vital Smart Cap however in the form of factor of a Sleeve which adheres to a standard bottle or container which may be replaceable, removed and used for a new or separate container, or The Vital Smart Base, an electronic base which fits on the bottom of a standard bottles or containers used throughout the healthcare industries. having all or some of the electronic capabilities of the Vital Smart Cap however in the form of factor of a Container Base which is attached to a standard bottle or container which may be replaceable, removed and used for a new or separate container or container which may be replaceable, removed and used for a new or separate container.

Cabinets or Boxes designed for Prescription Medicine, Vitamins or Supplements Product Interactions A standard medicine cabinet which is modified only by introducing an electromagnetic lock which is controlled by the Vital Smart Network through a smart phone or a fingerprint biometric reader controlling the locking mechanism.

A standard pill box designed for Prescription Medicine, Vitamins or Supplements modified to operate and or lock by the Vital Smart Network through a smart phone or a fingerprint biometric reader controlling the locking mechanism.

The electronic features included in the product iterations include hardware and firmware developed for contemporary biometric, wireless, RFID, linear bar coding, and bar code reading (of any sort) and which may be used with or without modern smart phone app technologies which further support the operation of any iteration of any of the apparatuses described.

Our suite of intellectual property is vital in the growing field of telemedicine and the realization and use of IoT (Internet of Things) technologies being implemented in modern product development.

There are over 4 Billion prescriptions filled in the United States every year using medicine bottles conforming to Child Resistant Packaging (CRP) international protocols.

The largest pharmacies in the world use the same bottle design in two cap form factors capping several sizes of bottles making these pharmacy bottles and caps more or less ubiquitous with two bottle cap sizes; Large and Small.

The ubiquitous design of the bottle used by this large market segment allows for a unique opportunity to solve many problems faced by the pharmaceutical industry as well as patient care and social issues including drug abuse and accidental overdose.

Vital is an electronic partner addition for existing medicine bottles whether prescription or otherwise.

All Vital products are currently designed to be implemented into the market place as consumer electronics devices where the consumer enjoys the security and assuredness of the technology by choice.

However, many of the technologies described within the suite of intellectual property are geared to move towards general practice over time.

Protect—There is a common problem in the United States and throughout the world where people experience the loss of their prescription medication by theft. Often times the main reason for the theft of prescription medications is the element of accessibility of the drug whether it is in a medicine cabinet, purse or simply hidden away in a drawer.

Vital helps to mitigate this problem with a Smart Lock. Replacing your cap with the Vital Smart Lock Cap is a simple cost-effective way to protect your medications from theft and or misuse.

The Vital Smart Lock Cap is an electronic locking cap which locks using fingerprint recognition biometrics using a fingerprint scanner on top of the (replacement) cap. The scanner authenticates the user via the fingerprint scan and then, using micro controllers, engages and disengages the locking cap mechanism. The security measure can be something other than a bio metric fingerprint scanner such as a numerical sequence that is chosen by the authorized user.

The locking cap mechanism is a methodology to interrupt the CRP bottle operation by mechanically interrupting the workability of the simple CRP procedure already perfected by the industry using universal design.

The cap is battery powered which is either rechargeable or replaceable depending on the technology and cost to pricing consideration. The locking mechanism may be programmed to disengage automatically when the battery is drained as an example of one of many safety precautions. This initial product is a standalone autonomous product meant for immediate introduction to the market place. (The "Sort of Smart Cap") As stated, the initial Vital Smart Lock Cap is not necessarily designed to communicate with a Smart Phone however when included in the Vital Smart Lock family of products, a "Connected Cap" connects to your smart phone which allows you to lock and unlock your medicine bottle using your smart phone through the Vital Health APP or EMT/Hospital override.

The product will also be released for the legal Medical Marijuana and Recreational Medical Marijuana industries under the trade name "Doc Pickett's Mustache" directly to dispensaries and smoke shops which continue to proliferate in modern society.

A variation of the product will be introduced to alcohol bottles for consumer use in homes. The Smart Lock Security Features are similar only instead of operating within the confines of the ubiquitous CRM cap the bottle stop will use a pressure cork bottle stop function which deems the bottle impenetrable. To aid in the longevity of the product currently described the product may incorporate the use of advanced micro fiber technologies. The locking bottle stop will be marketed under the trade name "Doc Pickett's Bottle Stop".

The cap has one LED light indicator which illuminates solid or blinks, under variable circumstances, either RED, GREEN, or YELLOW. The Smart Cap uses NFC near field communications, Bluetooth, or RFID. The Vital Smart Cap will be available with the lock feature and without the lock feature.

Protect—Contains the Locking Mechanism described in the Vital Smart Lock Cap with or without Biometric Fingerprint recognition scanner attribution. *Not all Vital Smart Caps Lock.

Identify—Using the Vital Health APP the user can "ask" to identify via voice command and or via the touch screen for the app to recognize the chosen medication. For instance, when you have the Vital Health App open you can say "Vital where is my blood pressure medicine" or "Vital where is my Atenolol" etc. either by brand name or category. You can also scroll through the list of your registered medications and simply click on the medication you are looking for. Once prompted the app sends a signal to the Vital Smart Cap and indicates the medication.

The voice recognition capability of the app also asks for visual verification prior to the light turning solid green. This function also works with the "Protect" function when and if the desired medication is secured with Vital Smart Lock.

Locate—Much like car keys and the television remote control it is a common problem for consumers to locate their medicine. With the Vital Smart Cap we accomplish discovering your medicine in one of two ways. When the user asks for a particular medicine from the Vital Health App the LED light will BLINK GREEN quickly until found or disengaged. Where possible the Cap will also make an audible noise with a Chirp at a frequency chosen for maximum attenuation and efficacy at range.

Remind—One of the biggest problems with maintaining any health regime is following through with the physicians prescribed regimen. This is a very serious problem in any prescription scenario and is especially troublesome when it comes to the use of antibiotics. Epidemiology shows that failure to follow the prescribed regimen when introducing antibiotics reduces the efficacy of the ability of the drug to fight disease and over time has affected our ability as human beings to stave off bacteria that are proving to be more and more impervious to antibiotics. ("The Super Bug")

Using the Vital Smart Cap the "Patient" or User is reminded to take their medicine on time and to complete the administration of the prescribed drug throughout the regimen or cycle. When you forget to take your medicine, the Vital Smart Cap Alerts you in three ways. It Blinks Yellow as you are getting close to the time for your medication and then blinks red and then sends a text message to remind you that it is time to take the medication. Then of course if you can't find it you simply ask it to Locate as described above.

Manage—All prescription bottles now include linear bar codes which identify the pharmacy, drug name, the manufacturer, the dosage, and expiration date. These barcodes have other information from the pharmacy that is confidential and may or not be accessed including patient ID, Date Filled, Refill Date and Refills Remaining for instance.

The Vital Health App will include a reader via any modern smart phone which can read the QRL code and then in turn add the medicine to the user's data base of medicines along with any prescribed regime of dispensing the medication.

This information will also be used to help the patient manage their health and wellness regime by reminding the patient much in the same way described above.

The App will also send the user a text when it is time to order their medication and at some point in time may include the ability to communicate with the pharmacy directly as systems are integrated for this purpose.

Figure 8:
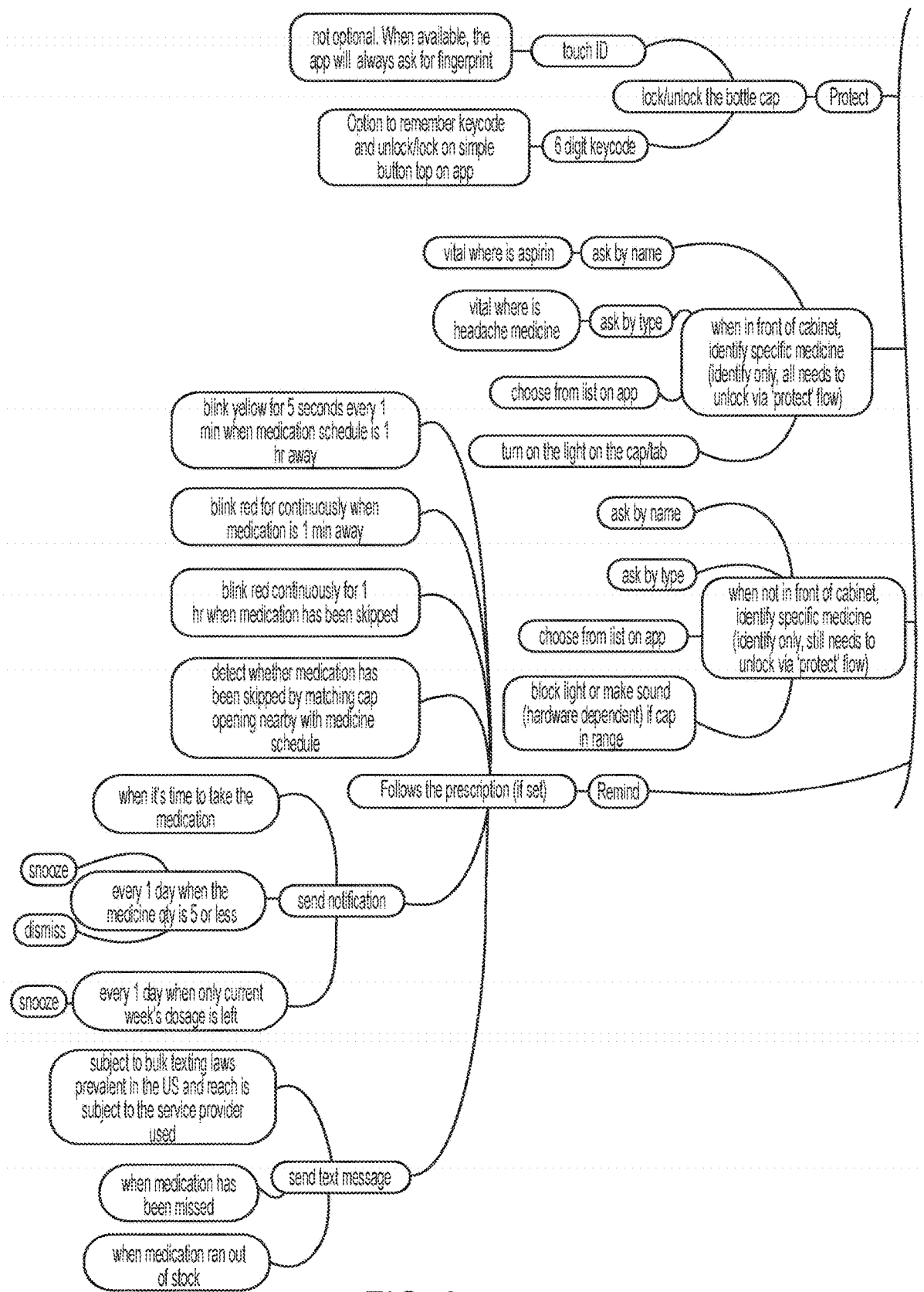
FIG. 8 shows a non-limiting example of a flowchart of a medication compliance application.
Figure 8:
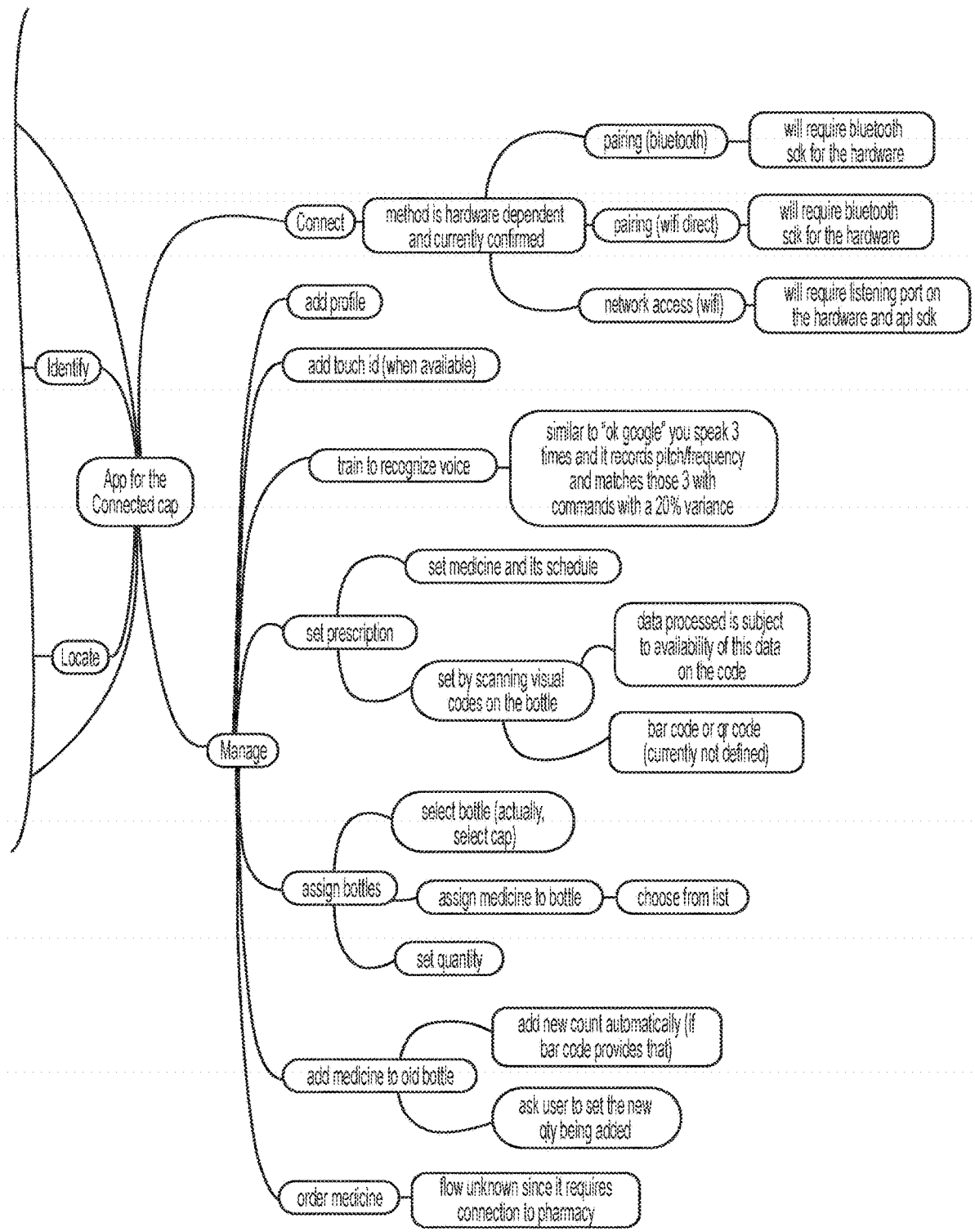
Figure 9:
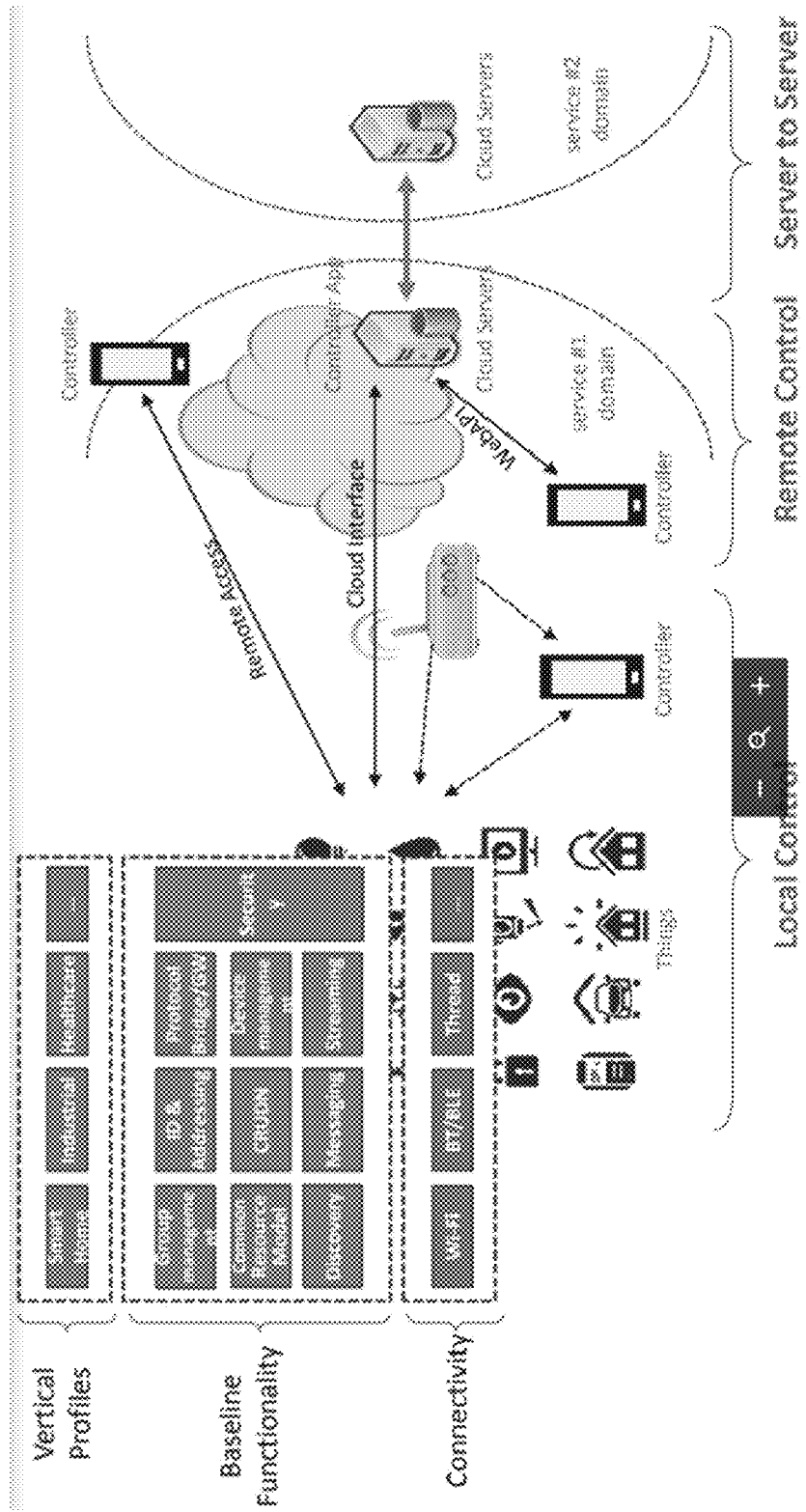
FIG. 9 shows a non-limiting example of a first medication compliance platform.
Figure 10:
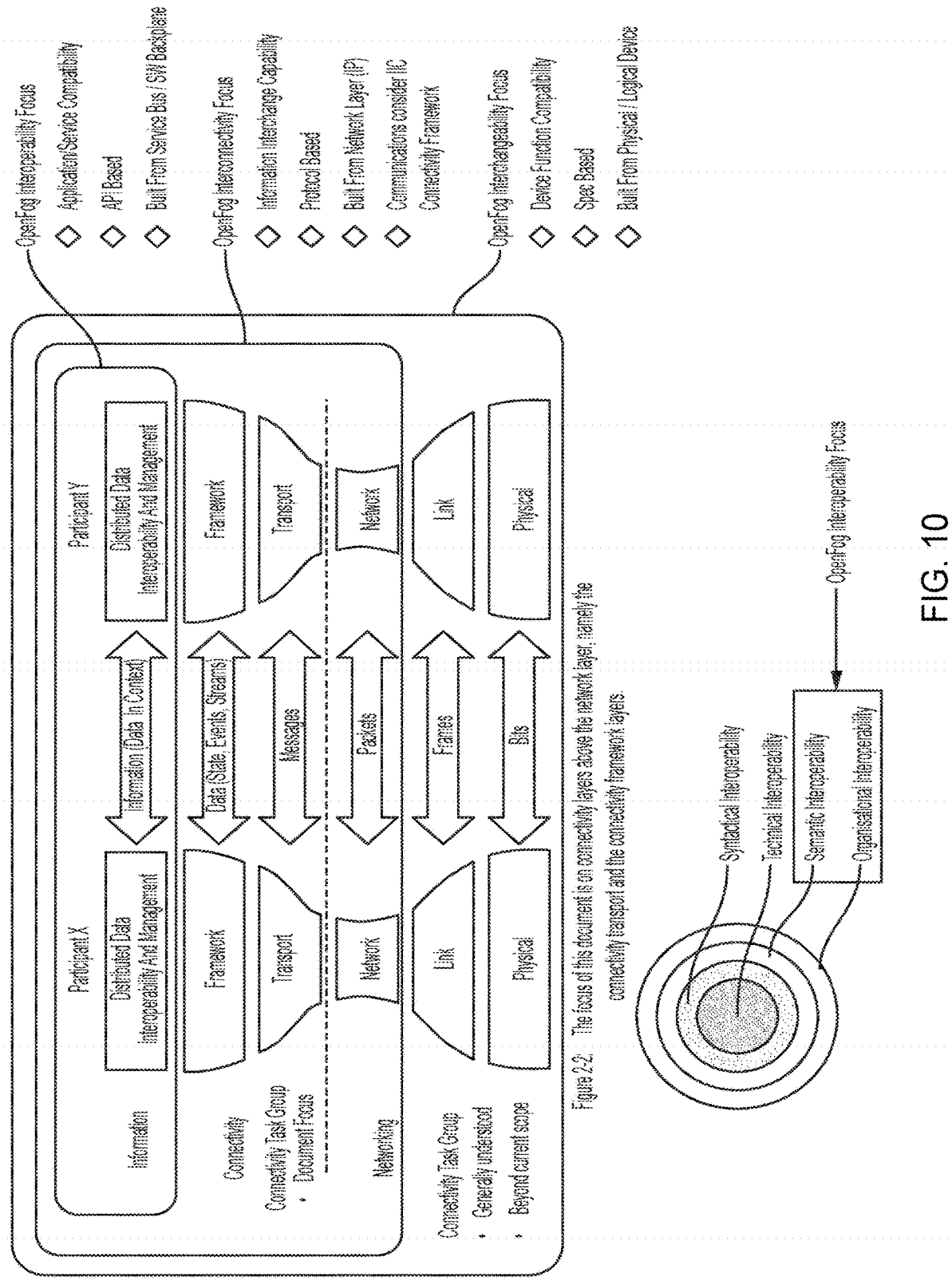
FIG. 10 shows a non-limiting example of a second medication compliance platform.
Figure 11:
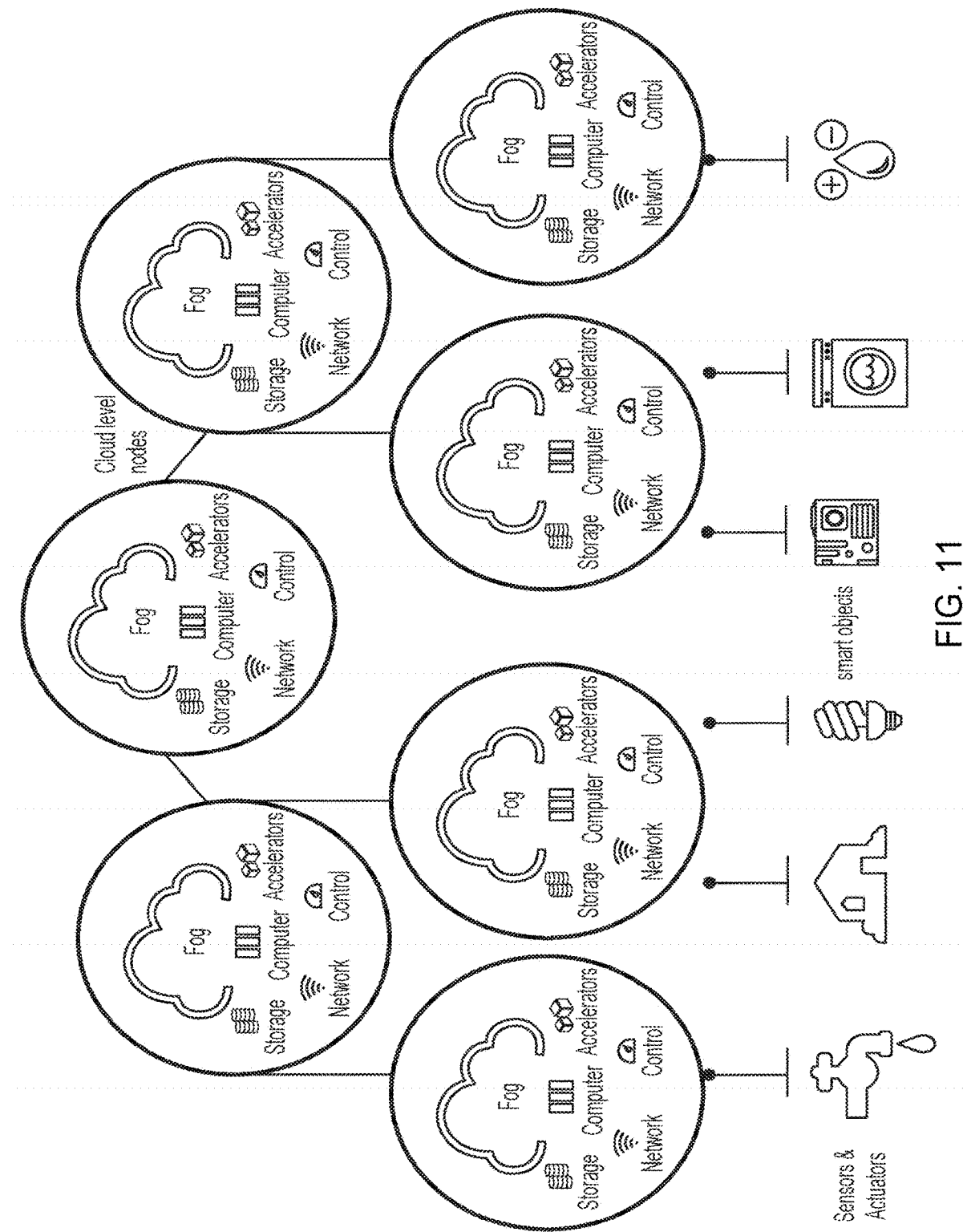
FIG. 11 shows a non-limiting example of a cloud of interconnected smart objects.

With a mechanical Locking Mechanism, (The Mechanical Locking Mechanism is achieved by one of many solutions including heat locks, electromagnetic controls and or mechanical geared slide locks) (FIG. 3.) or without a mechanical locking mechanism, or an autonomous Mechanical Locking Mechanism without the standard features of the Vital Smart Cap. An electronic strip or tab having all or some of the electronic capabilities of the Vital Smart Cap however in the form of factor of a strip or tab which adheres to a standard bottle or container which may be replaceable, removed and used for a new or separate container (FIG. 4.) or, an electronic sleeve whereby a standard bottle or container can be inserted and contained having all or some of the electronic capabilities of the Vital Smart Cap however in the form of factor of a Sleeve which adheres to a standard bottle or container which may be replaceable, removed and used for a new or separate container (FIG. 5.) or, an electronic base which fits on the bottom of a standard bottles or containers used throughout the healthcare industries. having all or some of the electronic capabilities of the Vital Smart Cap however in the form of factor of a Container Base which is attached to a standard bottle or container which may be replaceable, removed and used for a new or separate container or container which may be replaceable, removed and used for a new or separate container, (FIG. 6.) or, A standard medicine cabinet which is modified only by introducing an electromagnetic lock which is controlled by the Vital Smart Network through a smart phone or a fingerprint biometric reader controlling the locking mechanism. (FIG. 7.) A standard pill box designed for Prescription Medicine, Vitamins or Supplements modified to operate and or lock by the Vital Smart Network through a smart phone or a fingerprint biometric reader controlling the locking mechanism. (FIG. 8.)

EXAMPLES

The following illustrative examples are representative of embodiments of the software applications, systems, and methods described herein and are not meant to be limiting in any way.

Example 1—Medicine Identification

In one example of the present technology a smart medicament application is configured to locate a specific medicine. With the smart medicament application initialized and open, the user inputs information regarding medication name, a medical ailment, a medication dosage, a medication period, a medication interval, a doctor name, a patient name, a prescription date, a prescription number, a prescription barcode, a refill date, a number of refills, a pill size, a pill color. The user scans an additional medicine using a camera or handheld scanner. The user then uses a voice recognition command to request the location of a "blood pressure medicine." The application displays a medication associated with "blood pressure" and invites the user to confirm the selection. The application then sends a signal to the indicator of the smart medicament container cap, which lights up, vibrates, and emits a noise.

Example 2—Dosing Indication

In one example of the present technology a smart medicament application is configured to prevent accidental overdosing. The user enters a security data comprising a fingerprint to release the smart medicament container cap from a medicine bottle. The user removes a pill and locks the smart medicament container cap back onto the medicine bottle. A memory in the smart medicament container cap records the time that the cap was locked. Two hours later, the user enters a security data, the medication interval associated with that pill through the digital processing device is a six hour interval. The command module transmits a display data to the display screen comprising a notification that the medication interval has not been reached. The user can then override the notification with a password, pin, or with a mobile device.

Example 3—Method of Installing a Smart Medicament Container Cap

In one example of the present technology a smart medicament application is configured to replace a standard medicine bottle lid. To replace the lid of a standard medicine bottle, the user removes the lid, places a first cavity of the cap over an opening of the medicine bottle such that the radial array of the bottle engagement couplings align with the medicine bottle locking features. The user then twists the cap to align the bottle couplings on an interior surface of the cap with the recesses of the medicine bottle locking features. Upon submitting a security data comprising a fingerprint to the security input, the digital processing device recognizes the security data and transmits a command to the actuator, which advances the compression plate towards the standard medicine bottle. Once the compression plate firmly contacts an upper surface of the medicine bottle, the contents within the medicine bottle are temporarily locked.

Example 4—Method of Unlocking a Smart Medicament Container Cap

In one example of the present technology a smart medicament application is configured to be unlocked by a certified user. The user submits a security data comprising a fingerprint to the security input, whereby the digital processing device recognizes the security data and transmits a command to the actuator, which retracts the compression plate away the standard medicine bottle. The user then twists the cap to disengage the bottle couplings on an interior surface of the first cavity from the recesses of the medicine bottle locking features, and the cap can be removed to access the medication within the medicine bottle.

Example 5—Secure CBD Storage Container

*Cannabis* dispensaries often use the nondescript cylindrical pill bottles favored by pharmacies, often with a distinct green hue color instead of pharmacy-standard orange. Recognizing this issue, some states have adopted regulations requiring dispensaries to place *Cannabis* purchases in opaque, child-resistant pouches or bags. However, many consumers remove their *Cannabis* purchases from the child-resistant dispensary pouch and place them in a more accessible location at home.

In one example of the present technology a smart medicament container is configured for storing a CBD product such as an edible. As described above, the cap can be removed using a code and/or via a smart phone. For example, the user can release the smart medicament container cap with a code and/or fingerprint to open the bottle. The user can then remove an edible and lock the smart medicament container cap back onto the bottle. A memory in the smart medicament container cap records the time that the cap was locked. The user can review a record of dates/times that the container was accessed. In an embodiment, the user can also add a notation to indicate the volume or weight of product that was removed from the container. The user can also receive a notification if the cap or container has been tampered with.

While preferred embodiments of the present subject matter have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the subject matter described herein may be employed in practicing the invention.

What is claimed is:

1. A system for storing, securing and/or monitoring a *cannabis* product comprising:
   (a) a security input configured to receive a security data;
   (b) a digital processing device, wherein the digital processing device is configured to receive the security data from a security input;
   (c) a bottle comprising a sleeve engagement appendage; and
   (d) a smart medicament container cap comprising:
      (i) a housing comprising a bottle engagement coupling configured to engage with the sleeve engagement appendage;
      (ii) an actuator connected to the housing, the actuator controlled by the digital processing device in response to at least the security data; and
      (iii) a compression plate connected to the actuator and engaged with the housing by a slideable coupling;
   wherein the bottle engagement coupling, the actuator, and the compression plate are configured to temporarily prevent access to a *cannabis* product in the bottle and/or the bottle sleeve, and wherein the bottle is a pill container.

2. The system of claim 1, wherein security input is at least one of a keyhole, a button, a fingerprint scanner, a biometric scanner, a retinal scanner, a camera, a microphone, a GPS sensor, a Wi-Fi sensor, a Bluetooth sensor, an RFID sensor or a NFC sensor.

3. A method of managing consumption of a medicament or *cannabis* product using the system of claim 1.

4. The method of claim 3, wherein the *cannabis* product is an edible.

5. The system of claim 1, wherein the digital processing device is comprised of a wireless communication device configured to receive a wireless signal, and transmit a communications signal to the digital processing device, and wherein the communication signal is based on the wireless signal.

6. The system of claim 5, wherein the wireless signal comprises a medicament name, a medicament dosage, a medicament period, a medicament interval, a user name, a prescription date, a prescription number, a prescription barcode, a refill date, a number of refills, a dosage amount/size, a THC concentration, a CBD concentration, or any combination thereof.

* * * * *